US006410524B1

(12) United States Patent
Perez et al.

(10) Patent No.: US 6,410,524 B1
(45) Date of Patent: Jun. 25, 2002

(54) COMBINATION THERAPY OF ANGIOTENSIN CONVERTING ENZYME INHIBITOR AND ALDOSTERONE ANTAGONIST FOR REDUCING MORBIDITY AND MORTALITY FROM CARDIOVASCULAR DISEASE

(75) Inventors: Alfonzo T. Perez, Lake Forest; Debra J. Asner, Morton Grove; Richard J. LaChapelle, Wilmette, all of IL (US); John C. Alexander, Princeton, NJ (US); Barbara Roniker, Chicago, IL (US)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 09/434,685

(22) Filed: Nov. 5, 1999

Related U.S. Application Data

(60) Provisional application No. 60/107,398, filed on Nov. 6, 1998, provisional application No. 60/122,977, filed on Mar. 5, 1999, and provisional application No. 60/122,978, filed on Mar. 5, 1999.

(51) Int. Cl.⁷ ............................................. A61K 31/585
(52) U.S. Cl. ..................................................... 514/175
(58) Field of Search ......................................... 514/175

(56) References Cited

U.S. PATENT DOCUMENTS

| | | | |
|---|---|---|---|
| 3,257,390 A | 6/1966 | Patchett | |
| 4,129,564 A | * 12/1978 | Wiechert et al. | ............. 514/175 |
| 4,559,332 A | * 12/1985 | Grob et al. | ................. 514/175 |
| 4,789,668 A | 12/1988 | Nickisch et al. | |

FOREIGN PATENT DOCUMENTS

| | | | |
|---|---|---|---|
| WO | 96/24358 | * 8/1996 | ................. 514/175 |
| WO | WO9624372 | 8/1996 | |
| WO | 96/24372 | * 8/1996 | ................. 514/175 |
| WO | WO9624373 | 8/1996 | |
| WO | 96/24373 | * 8/1996 | ................. 514/175 |
| WO | WO9640255 | 12/1996 | |
| WO | 9640256 | 12/1996 | |

OTHER PUBLICATIONS

Mantero et al, *Clin. Sci.Mol.Med.*, 45 (Suppl.1) :219s–224s (1973).
Saunders et al., *Aldactone;Spironolactone: Comprehens.Review* (1978).
Greenberger et al., *N.Eng.Reg.Allergy Proc.* 7: 4 343–345 (Jul–Aug.1986).
Klug et al., *Am.J.Cardiol.* 71 (3) 46A–54A (1993).
Brilla et al., *J.Mol.Cell.Cardiol.* 25:5 563–575 (1993).
Phys.Desk Ref., 46th Edn.,p.2153.Med.Econ.Company,Inc., N.J. (1992).
Staessen et al., *J. Endocrin.*, 91, 457–465 (1981).
Borghi et al., *J. Clin.Pharmacol.*, 33 40–45 (1993).
Poncelet et al, *Am.J.Cardiol.*, 65 (2), 33K–35K (1990).
Dahlstrom et al, *Am.J.Cardiol.*, 71, 29A–33A (Jan. 21, 1993).
VanVliet et al.,*Am.J.Cardiol.*, 91, 21A–28A (Jan. 21, 1993).
F. Zannad., *Am.J.Cardiol.*, 71 (3), 34A–39A (1993).
Brilla et al., *Schweiz Rundsch Med Prax*, 86 (14) :566–574 (Apr. 2, 1997).
Rodriguez A et al, *Rev Med Chil*, 125 (6) :643–52 1997 (Jun. 1997).
Beneto et al, *Arterioscler Thromb Vasc Biol*, 17 (6) :1152–6 (Jun. 1997).
Araki et al, *Jpn Circ J*, 59 (4) :213–8 (Apr. 1995).
Hensen et al, *Am J Nephrol*, 11 (6) :441–6 (1991).
Nicoletti et al, *Hypertension*, 26 (1) :101–11 (Jul. 1995).
van Vilet et al, *Am J Cardiol*, 71 (3) :21A–28A (Jan. 21, 1993).
Brown L et al, *J Am Soc Nephrol*, 10 Suppl 11 :S143–8 (Jan. 1999).
Follath, *Eur Heart J*, 19 Suppl P :P5–8 (Dec. 1998).
Klauber et al, *Circulation*, vol94 (10) :2566–2571 (Nov. 1996).
Pitt, *Cardiovasc Drugs Ther*, 9 (1) :145–9.
Ikram, et al, *Aust N Z J Med*, 16 (1) :61–3 (Feb. 1986).
Yasky et al, *Pharmatherapeutica*, 4 (8) :480–5 (1986).
Rodriguez et al, *Rev Med Chil*, 125 (6_:643–52 (Jun. 1997).
Halawa, *Pol Merkuriusz Lek*, 4 (19) :32–4 (Jan. 1998).
Kinugawa et al, *General Pharmacology*, 31 (1) :93–99 (1998).
Dyckner, *Am J Cardiol*, 65 (23) :44K–46K (Jun. 19, 1990).
Khan, *Can Med Assoc J*, 123 (9) :883–7 (Nov. 1980).
Packer et al, *J Am Coll Cardial*, 7 (3) :671–80 (Mar. 1986).
Dueymes, *Am J Cardial*, 65 (23) :20K–23K (Jun. 1990).
Brilla et al, *Am J Cardiol*, 71 (3) :12A–16A (Jan. 21, 1993).
Barr et al, *Am J Cardiol*, 76 (17) :1259–65 (Dec. 1995).
Blacher et al, *Am J Hypertens*, 10 (12Ptl) :1326–34 (Dec. 1997).
Pasquale et al, *Clin Drug Invest* 17 (5) :347–355 (1999).
Yasky et al, *Pharmatherapeutica*, 4 (8) :473–9 (1986).
Denis et al, *Arch Mal Coeur Vaiss*, 77 Spec No:35–40 (1984).
Lauler, *Am J Cardiol*, 65 (23) :18K–19K (Jun. 19, 1990).

\* cited by examiner

*Primary Examiner*—James H. Reamer
(74) *Attorney, Agent, or Firm*—G. D. Searle & Co.; J. Timothy Keane; Joseph R. Schuh

(57) ABSTRACT

Combinations of an ACE inhibitor, an aldosterone antagonist, and a loop diuretic are described for use in treatment of circulatory disorders. Of particular interest are therapies using captopril, enalapril or lisinopril co-administered with spironolactone. This co-therapy would be particularly useful to reduce the death rate or the number of non-fatal hospitalizations or prevent the progression of congestive heart failure in patients with cardiovascular disease.

105 Claims, 8 Drawing Sheets

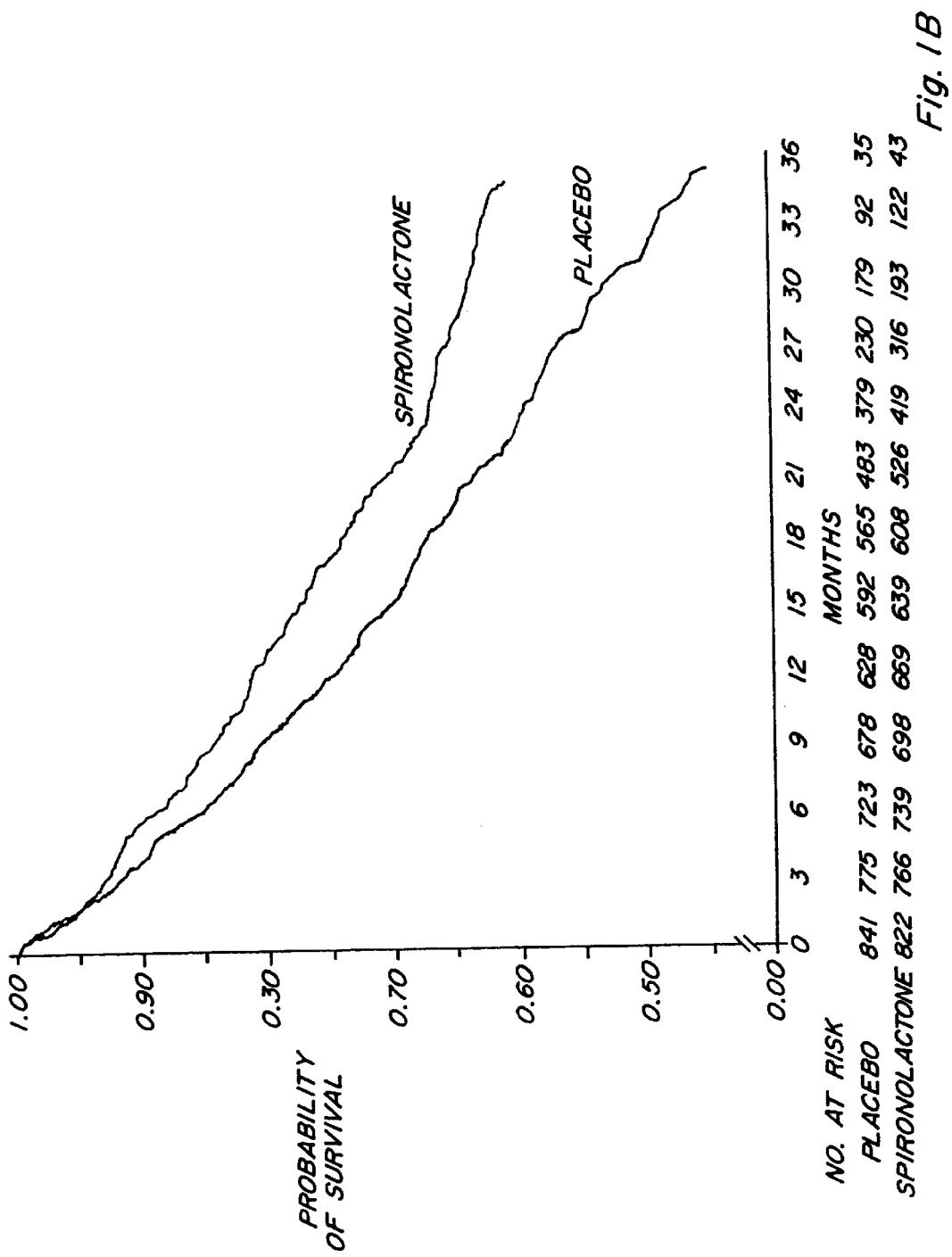

RISK REDUCTION FOR TOTAL MORTALITY BY BASELINE GROUP

|  | RISK REDUCTION | 95% CI FOR RISK REDUCTION |
|---|---|---|
| MEDIAN AGE (YEARS) | | |
| ≤67 | 0.23 | (0.40, 0.01) |
| ≥67 | 0.28 | (0.41, 0.11) |
| LEFT VENTRICULAR EJECTION FRACTION (%) | 0.18 | (0.34, -0.01) |
| ≤26 | 0.35 | (0.49, 0.17) |
| ≥26 | | |
| ETIOLOGY OF HEART FAILURE | | |
| NON-ISCHEMIC | 0.30 | (0.45, 0.10) |
| ISCHEMIC | 0.24 | (0.38, 0.06) |
| CREATININE MEDIAN (μmol/L) | | |
| ≤106.0 | 0.37 | (0.51, 0.18) |
| ≥106.0 | 0.18 | (0.33, -0.01) |
| DIGITALIS | | |
| NO | 0.13 | (0.37, -0.18) |
| YES | 0.31 | (0.42, 0.17) |
| ACE INHIBITORS | | |
| NO | 0.04 | (0.41, -0.56) |
| YES | 0.28 | (0.40, 0.15) |
| SEX | | |
| FEMALE | 0.26 | (0.47, -0.02) |
| MALE | 0.26 | (0.39, 0.12) |
| POTASSIUM MEDIAN (mmol/L) | | |
| ≤4.2 | 0.27 | (0.43, 0.06) |
| ≥4.2 | 0.25 | (0.40, 0.08) |
| NYHA | | |
| CLASS III | 0.25 | (0.39, 0.08) |
| CLASS IV | 0.24 | (0.41, 0.01)0 |

Fig. 2

COMBINATION THERAPY OF ANGIOTENSIN CONVERTING ENZYME INHIBITOR AND ALDOSTERONE ANTAGONIST FOR REDUCING MORBIDITY AND MORTALITY FROM CARDIOVASCULAR DISEASE

CROSS-REFERENCE TO RELATED APPLICATIONS

This application claims priority from U.S. provisional patent application Ser. No. 60/107,398 filed on Nov. 6, 1998; U.S. provisional patent application Ser. No. 60/122,977 filed on Mar. 5, 1999, U.S. provisional patent application Ser. No. 60/122,978 filed on Mar. 5, 1999. Each of these priority applications is specifically incorporated herein by reference.

FIELD OF THE INVENTION

Combinations of an angiotensin converting enzyme inhibitor and an aldosterone antagonist are described for use in treatment of circulatory disorders, including cardiovascular diseases such as heart failure, hypertension and congestive heart failure. Of particular interest are therapies using a spirolactone-type aldosterone antagonist compound in combination with an angiotensin converting enzyme inhibitor to reduce the death rate or the number of non-fatal hospitalizations in patients.

BACKGROUND OF THE INVENTION

Myocardial (or cardiac) failure, that is, heart failure ("HF"), whether a consequence of previous myocardial infarction(s), heart disease associated with hypertension, or primary cardiomyopathy, is a major health problem of worldwide proportions. The incidence of symptomatic heart failure has risen steadily over the past several decades.

In clinical terms, decompensated cardiac failure consists of a constellation of signs and symptoms that arise from congested organs and poorly perfused tissues to form congestive heart failure (CHF) syndrome. Congestion is caused largely by increased venous pressure and by inadequate sodium ($Na^+$) excretion, relative to dietary $Na^+$ intake, and is importantly related to circulating levels of aldosterone (ALDO). An abnormal retention of $Na^+$ occurs via tubular epithelial cells throughout the nephron, including the later portion of the distal tubule and cortical collecting ducts, where ALDO receptor sites are present.

ALDO is the body's most potent mineralocorticoid hormone. As implied by the term mineralocorticoid, this steroid hormone has mineral-regulating activity. It promotes $Na^+$ reabsorption not only in the kidney, but also from the lower gastrointestinal tract and salivary and sweat glands, each of which represents classic ALDO-responsive tissues. ALDO regulates $Na^+$ and water resorption at the expense of potassium ($K^+$) and magnesium ($Mg^{2+}$) excretion.

ALDO can also provoke responses in non-epithelial cells. Elicited by a chronic elevation in plasma ALDO level that is inappropriate relative to dietary $Na^+$ intake, these responses can have adverse consequences on the structure of the cardiovascular system. Hence, ALDO can contribute to the progressive nature of myocardial failure for multiple reasons.

Multiple factors regulate ALDO synthesis and metabolism, many of which are operative in the patient with myocardial failure. These include renin as well as non-renin-dependent factors (such as $K^+$, ACTH) that promote ALDO synthesis. Hepatic blood flow, by regulating the clearance of circulating ALDO, helps determine ALDO plasma concentration, an important factor in heart failure characterized by reduction in cardiac output and hepatic blood flow.

The renin-angiotensin-aldosterone system ("RAAS") is one of the hormonal mechanisms involved in regulating pressure/volume homeostasis and also in the development of hypertension, a precursor condition implicated in the progression of more serious cardiovascular diseases such as congestive heart failure. Activation of the renin-angiotensin-aldosterone system begins with secretion of the enzyme renin from the juxtaglomerular cells in the kidney. The enzyme renin acts on a naturally-occurring substrate, angiotensinogen, to release a decapeptide, Angiotensin I. This decapeptide is cleaved by angiotensin converting enzyme ("ACE") to provide an octapeptide, Angiotensin II, the primary active species of this system. This octapeptide, angiotensin II, is a potent vasoconstrictor and also produces other physiological effects such as stimulating aldosterone secretion, promoting sodium and fluid retention, inhibiting renin secretion, increasing sympathetic nervous system activity, stimulating vasopressin secretion, causing a positive cardiac inotropic effect and modulating other hormonal systems.

Emphasis has been placed on minimizing hyperaldosteronism as a basis for optimizing patient treatment. This includes the importance of ALDO-receptor antagonism both in patients treated with conventional diuretic programs and in patients treated with angiotensin-converting enzyme (ACE) inhibitors, who are often constrained to small doses of ACE inhibitor because of orthostatic hypotension. Such patients may demonstrate a recurrence of heart failure symptoms likely related to elevations in plasma ALDO levels.

Many aldosterone blocking drugs and their effects in humans are known. For example, spironolactone is a drug which acts at the mineralocorticoid receptor level by competitively inhibiting aldosterone binding. This steroidal compound has been used for blocking aldosterone-dependent sodium transport in the distal tubule of the kidney in order to reduce edema and to treat essential hypertension and primary hyperaldosteronism [F. Mantero et al, *Clin. Sci. Mol. Med.*, 45 (Suppl 1), 219s–224s (1973)]. Spironolactone is also used commonly in the treatment of other hyperaldosterone-related diseases such as liver cirrhosis and congestive heart failure [F. J. Saunders et al, *Aldactone; Spironolactone: A Comprehensive Review*, Searle, New York (1978)]. Progressively-increasing doses of spironolactone from 1 mg to 400 mg per day [i.e., 1 mg/day, 5 mg/day, 20 mg/day] were administered to a spironolactone-intolerant patient to treat cirrhosis-related ascites [P. A. Greenberger et al, *N. Eng. Reg. Allergy Proc.*, 7(4), 343–345 (July–August, 1986)]. It has been recognized that development of myocardial fibrosis is sensitive to circulating levels of both Angiotensin II and aldosterone, and that the aldosterone antagonist spironolactone prevents myocardial fibrosis in animal models, thereby linking aldosterone to excessive collagen deposition [D. Klug et al, *Am. J. Cardiol.*, 71(3), 46A–54A (1993)]. Spironolactone has been shown to prevent fibrosis in animal models irrespective of the development of left ventricular hypertrophy and the presence of hypertension [C. G. Brilla et al, *J. Mol. Cell. Cardiol.*, 25(5), 563–575 (1993)]. Spironolactone at a dosage ranging from 25 mg to 100 mg daily is used to treat diuretic-induced hypokalemia, when orally-administered potassium supplements or other potassium-sparing regimens are considered inappropriate [Physicians' Desk Reference, 46th Edn., p. 2153, Medical Economics Company Inc., Montvale, N.J. (1992)].

Previous studies have shown that inhibiting ACE inhibits the renin-angiotensin system by substantially complete blockade of the formation of Angiotensin II. Many ACE inhibitors have been used clinically to control hypertension. While ACE inhibitors may effectively control hypertension, side effects are common including chronic cough, skin rash, loss of taste sense, proteinuria and neutropenia.

Moreover, although ACE inhibitors effectively block the formation of Angiotensin II, aldosterone levels are not well controlled in certain patients having cardiovascular diseases. For example, despite continued ACE inhibition in hypertensive patients receiving captopril, there has been observed a gradual return of plasma aldosterone to baseline levels [J. Staessen et al, *J. Endocrinol.*, 91, 457–465 (1981)]. A similar effect has been observed for patients with myocardial infarction receiving zofenopril [C. Borghi et al, *J. Clin. Pharmacol.*, 33, 40–45 (1993)]. This phenomenon has been termed "aldosterone escape".

Combinations of an aldosterone antagonist and an ACE inhibitor have been investigated for treatment of heart failure. It is known that mortality is higher in patients with elevated levels of plasma aldosterone and that aldosterone levels increase as CHF progresses from RAAS activation. Routine use of a diuretic may further elevate aldosterone levels. ACE inhibitors consistently inhibit angiotensin II production but exert only a mild and transient antialdosterone effect.

Combining an ACE inhibitor and spironolactone has been suggested to provide substantial inhibition of the entire RAAS. For example, a combination of enalapril and a 25 mg daily dose of spironolactone has been administered to ambulatory patients with monitoring of blood pressure [P. Poncelet et al, *Am. J. Cardiol.*, 65(2), 33K–35K (1990)]. In a 90-patient study, a combination of spironolactone at a dose in a range from 50 mg/day to 100 mg/day (average 73 mg/day) and captopril was administered and found effective to control refractory CHR without serious incidents of hyperkalemia [U. Dahlstrom et al, *Am. J. Cardiol.*, 71, 29A–33A (Jan. 21, 1993)]. Spironolactone dosage at 100 mg/day coadministered with an ACE inhibitor was reported to be highly effective in 13 of 16 patients afflicted with congestive heart failure, with a 25 mg/day to 50 mg/day spironolactone maintenance dosage given at trial completion to compensated patients being treated with an ACE inhibitor and loop diuretic [A. A. van Vliet et al, *Am. J. Cardiol.*, 71, 21A–28A (Jan. 21, 1993)]. Clinical improvements have been reported for patients receiving a co-therapy of spironolactone and the ACE inhibitor enalapril, although this report mentions that controlled trials are needed to determine the lowest effective doses and to identify which patients would benefit most from combined therapy [F. Zannad, *Am. J. Cardiol.*, 71(3), 34A–39A (1993)].

Spironolactone, in combination with ACE inhibitors and loop diuretic therapy, has been shown to be effective in reducing N-terminal pro-atrial natriuretic factor, a marker of heart failure, in patients with that disease [The RALES Investigators, *Am. J. Cardiol.*, 78(8), 902–907 (1996)].

Low dosages of spironolactone (e.g., less than 25 mg per day) for use in treating cardiovascular diseases such as hypertension and heart failure, are described in PCT Application WO 96/24358, published Aug 15, 1996.

Combination of an ACE inhibitor and low dosages of spironolactone (less than 25 mg per day) for treating congestive heart failure are described in PCT Application WO 96/24373, published Aug 15, 1996.

Use of combinations of ACE inhibitors, low dosages of spironolactone (less than 25 mg/day) and diuretic agents for treating congestive heart failure, are described in PCT Application WO 96/24372, published Aug. 15, 1996.

SUMMARY OF THE DRAWING FIGURES

FIG. 1B shows an audited analysis using the Kaplan-Meier method of mortality among patients with severe heart failure in placebo and spironolactone treated groups. Both groups were co-administered stable doses of an ACE inhibitor and a loop diuretic.

FIG. 2 shows the risk reduction in mortality and 95% confidence interval for patients treated with spironolactone co-therapy, according to various baseline (pre-randomization) variables.

DESCRIPTION OF THE INVENTION

Figure 1A:
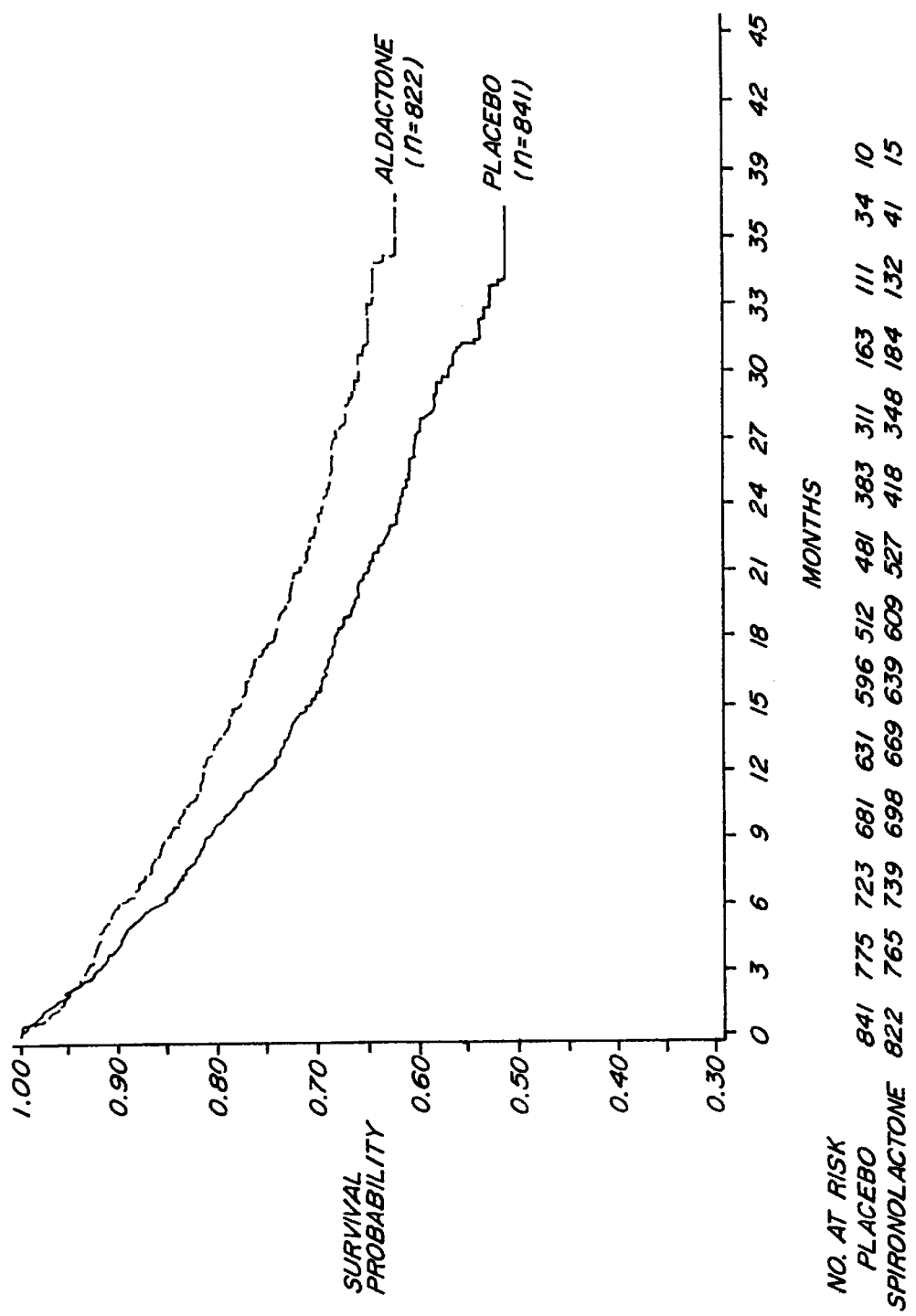
FIG. 1A shows a preliminary Kaplan-Meier analysis of mortality among patients with severe heart failure in placebo and spironolactone treated groups. Both groups were co-administered stable doses of an ACE inhibitor and a loop diuretic.

Treatment or prevention of circulatory disorders, including cardiovascular disorders such as heart failure, hypertension and congestive heart failure, is provided by a combination therapy comprising a therapeutically-effective amount of an angiotensin converting enzyme ("ACE") inhibitor along with a therapeutically-effective amount of a spirolactone-type aldosterone antagonist. Preferably, the combination therapy comprises administering therapeutically effective amounts of an ACE inhibitor, an aldosterone antagonist, and a diuretic wherein the diuretic has no substantial aldosterone receptor antagonistic effect.

The combination therapy of the invention would be useful, for example, to reduce the death rate or the number of non-fatal hospitalizations or to prevent or retard, in subjects, the development of congestive heart failure which typically arises from essential hypertension or from heart conditions following myocardial infarct. A diuretic agent may also be used in conjunction with an ACE inhibitor and an aldosterone antagonist.

Alternatively, the combination therapy can comprise administering an angiotensin converting enzyme inhibitor, an aldosterone antagonist and a loop diuretic to the subject, wherein the angiotensin converting enzyme inhibitor, the aldosterone antagonist and the loop diuretic are administered at doses that in combination result in one or more of the following (1) a statistically significant reduction in the death rate as compared to said combination therapy without the aldosterone antagonist (2) a statistically significant reduction in the number of non-fatal hospitalizations as compared to said combination therapy without the aldosterone antagonist; (3) a statistically significant reduction in the death rate or the number of non-fatal hospitalizations as compared to said combination therapy without the aldosterone antagonist; (4) a statistically significant reduction in the rate of deaths resulting from sudden death in subjects afflicted with or susceptible to elevated heart rate variability as compared to said combination therapy without the aldosterone antagonist; (5) a statistically significant reduction in the death rate for deaths resulting from progression of heart failure as compared to said combination therapy without the aldosterone antagonist; (6) a statistically significant reduction in the death rate or the number of non-fatal hospitalizations in subjects having a left ventricular ejection fraction greater than about 26% as compared to said combination therapy without the aldosterone antagonist; (7) a statistically significant reduction in the death rate or the number of non-fatal hospitalizations in subjects having a left ventricular ejection fraction less than about 26% as compared to said combination therapy without the aldosterone antagonist; and/or (8) suppression of clinically significant cough due to elevated pulmonary arterial fibrosis or low levels of pulmonary blood pressure in the subject as compared to said combination therapy.

Still alternatively, the combination therapy may comprise administering a therapeutically-effective amount of an angiotensin converting enzyme inhibitor, a therapeutically-effective amount of an aldosterone antagonist, a therapeutically-effective amount of a loop diuretic and a therapeutically-effective amount of digoxin to the subject.

Preferably, the subject receiving the combination therapy: (1) is susceptible to sudden death; (2) is classified in New York Heart Association class III or class IV prior to combination therapy; (3) has a left ventricular ejection fraction greater than about 26%; and/or (4) is susceptible to or suffering from clinically significant cough due to elevated pulmonary arterial fibrosis or low levels of pulmonary blood pressure. The phrase "angiotensin converting enzyme inhibitor" ("ACE inhibitor") is intended to embrace an agent or compound, or a combination of two or more agents or compounds, having the ability to block, partially or completely, the rapid enzymatic conversion of the physiologically inactive decapeptide form of angiotensin ("Angiotensin I") to the vasoconstrictive octapeptide form of angiotensin ("Angiotensin II"). Blocking the formation of Angiotensin II can quickly affect the regulation of fluid and electrolyte balance, blood pressure and blood volume, by removing the primary actions of Angiotensin II. Included in these primary actions of Angiotensin II are stimulation of the synthesis and secretion of aldosterone by the adrenal cortex and raising blood pressure by direct constriction of the smooth muscle of the arterioles.

The phrase "aldosterone antagonist" embraces an agent or compound, or a combination of two or more of such agents or compounds, which counteract the effect of aldosterone. Such agents and compounds, such as mespirenone, may antagonize the action of aldosterone through pre-receptor mechanism. Other agents and compounds, such as spironolactone and eplerenone, fall generally within a class known as aldosterone receptor antagonists and bind to aldosterone receptors such as typically are found in renal tubules, and prevent natural ligand activation of post-receptor events.

The term "spirolactone-type" is intended to characterize a steroidal structure comprising a lactone moiety attached to a steroid nucleus, typically at the steroid "D" ring, through a spiro bond configuration. A subclass of spirolacton-type aldosterone antagonist consists of epoxy-steroidal aldosterone antagonist compounds such as eplerenone. Another subclass of spirolactone-type antagonist consists of non-epoxy-steroidal aldosterone antagonist compounds such as spironolactone.

The phrase "combination therapy" (or "co-therapy"), in defining use of an ACE inhibitor agent, an aldosterone antagonist agent, loop diuretic agent, and/or digoxin is intended to embrace administration of each agent in a sequential manner in a regimen that will provide beneficial effects of the drug combination, and is intended as well to embrace co-administration of these agents in a substantially simultaneous manner, such as by oral ingestion of a single capsule having a fixed ratio of these active agents or ingestion of multiple, separate capsules for each agent. "Combination therapy" will also include simultaneous or sequential administration by intravenous, intramuscular or other parenteral routes into the body, including direct absorption through mucuous membrane tissues, as found in the sinus passages. Sequential administration also includes drug combination where the individual elements may be administered at different times and/or by different routes but which act in combination to provide a beneficial effect.

The phrase "therapeutically-effectve" is intended to qualify the amount of each agent for use in the combination therapy which will achieve the goal of improvement in cardiac sufficiency by reducing or preventing, for example, the progression of congestive heart failure, while avoiding adverse side effects typically associated with each agent.

A preferred combination therapy would consist essentially of two active agents, namely, an ACE inhibitor agent and aldosterone antagonist agent. The agents would be used in combination in a weight ratio range from about 0.5-to-one to about twenty-to-one of the angiotensin converting enzyme agent to the aldosterone antagonist agent. A preferred range of these two agents (ACE inhibitor-to-ALDO antagonist) would be from about one-to-one to about fifteen-to-one, while a more preferred range would be from about one-to-one to about five-to-one, depending ultimately on the selection of the ACE inhibitor and ALDO antagonist. A more preferred combination therapy would consist essentially of three active agents, namely, an ACE inhibitor agent, an aldosterone antagonist agent, and a loop diuretic agent.

Examples of ACE inhibitors which may be used in the combination therapy are shown in the following categories.

A representative group of ACE inhibitors consists of the following compounds: AB-103, ancovenin, benazeprilat, BRL-36378, BW-A575C, CGS-13928C, CL-242817, CV-5975, Equaten, EU-4865, EU-4867, EU-5476, foroxymithine, FPL 66564, FR-900456, Hoe-065, I5B2, indolapril, ketomethylureas, KRI-1177, KRI-1230, L-681176, libenzapril, MCD, MDL-27088, MDL-27467A, moveltipril, MS-41, nicotianamine, pentopril, phenacein, pivopril, rentiapril, RG-5975, RG-6134, RG-6207, RGH-0399, ROO-911, RS-10085-197, RS-2039, RS 5139, RS 86127, RU-44403, S-8308, SA-291, spiraprilat, SQ-26900, SQ-28084, SQ-28370, SQ-28940, SQ-31440, Synecor, utibapril, WF-10129, Wy-44221, Wy-44655, Y-23785, Yissum P-0154, zabicipril, Asahi Brewery AB-47, alatriopril, BMS 182657, Asahi Chemical C-111, Asahi Chemical C-112, Dainippon DU-1777, mixanpril, Prentyl, zofenoprilat, 1-(-(1-carboxy-6-(4-piperidinyl)hexyl)amino)-1-oxopropyl octahydro-1H-indole-2-carboxylic acid, Bioproject BP1.137, Chiesi CHF 1514, Fisons FPL-66564, idrapril, Marion Merrell Dow MDL-100240, perindoprilat and Servier S-5590, alacepril, benazepril, captopril, cilazapril, delapril, enalapril, enalaprilat, fosinopril, fosinoprilat, imidapril, lisinopril, perindopril, quinapril, ramipril, saralasin acetate, temocapril, trandolapril, ceranapril, moexipril, quinaprilat and spirapril.

A group of ACE inhibitors of high interest consists of the following compounds: alacepril, benazepril, captopril, cilazapril, delapril, enalapril, enalaprilat, fosinopril, fosinoprilat, imidapril, lisinopril, perindopril, quinapril, ramipril, saralasin acetate, temocapril, trandolapril, ceranapril, moexipril, quinaprilat and spirapril.

Many of these ACE inhibitors are commercially available, especially those listed in the above group. For example, a highly preferred ACE inhibitor, captopril, is sold by E. R. Squibb & Sons, Inc., Princeton, N.J., now part of Bristol-Myers-Squibb, under the trademark "CAPOTEN", in tablet dosage form at doses of 12.5 mg, 50 mg and 100 mg per tablet. Enalapril or Enalapril Maleate, and Lisinopril are two more highly preferred ACE inhibitors sold by Merck & Co, West Point, Pa. Enalapril is sold under the trademark "VASOTEC" in tablet dosage form at doses of 2.5 mg, 5 mg, 10 mg and 20 mg per tablet. Lisinopril is sold under the trademark "PRINIVIL" in tablet dosage form at doses of 5 mg, 10 mg, 20 mg and 40 mg per tablet.

A family of spirolactone-type compounds of interest is defined by Formula I

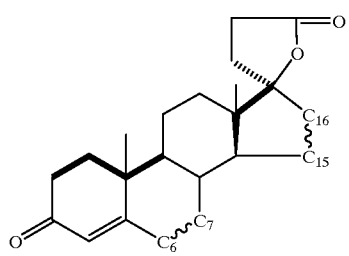

(I)

wherein

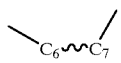

is

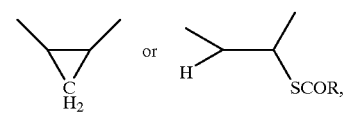

wherein R is lower alkyl of up to 5 carbon atoms, and wherein

is

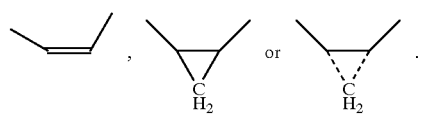

Lower alkyl residues include branched and un-branched groups, preferably methyl, ethyl and n-propyl.

Specific compounds of interest within Formula I are the following:

7α-Acetylthio-3-oxo-4,15-androstadiene-[17(β-1')-spiro-5'] perhydrofuran-2'-one;

3-Oxo-7α-propionylthio-4,15-androstadiene-[17((β-1')-spiro-5']perhydrofuran-2'-one;

6β,7β-Methylene-3-oxo4,15-androstadiene-[17((β-1')-spiro-5']perhydrofuran-2'-one;

15α,16α-Methylene-3-oxo-4,7α-propionylthio-4-androstene[17(β-1')-spiro-5']perhydrofuran-2'-one;

6β,7β,15α,16α-Dimethylene-3-oxo-4-androstene [17(β-1')-spiro-5']perhydrofuran-2'-one;

7α-Acetylthio-15β,16β-Methylene-3-oxo-4-androstene [17 (β-1')-spiro-5']perhydrofuran-2'-one;

15β,16β-Methylene-3-oxo-7β-propionylthio-4-androstene-[17(β-1')-spiro-5']perhydrofuran-2'-one; and 6β,7β,15β,16β-Dimethylene-3-oxo-4-androstene-[17(β-1')-spiro-5']perhydrofuran-2'-one.

Methods to make compounds of Formula I are described in U.S. Pat. No. 4,129,564 to Wiechart et al issued on Dec. 12, 1978.

A second family of spirolactone-type compounds of interest is defined by Formula II:

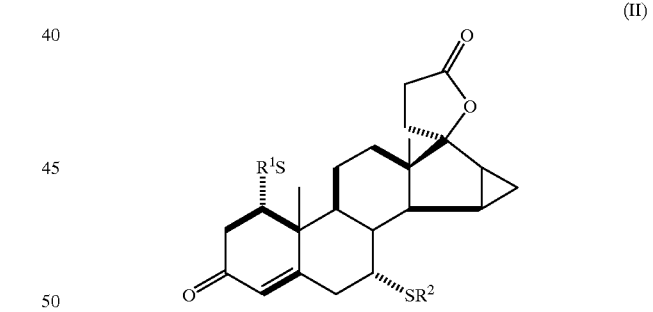

(II)

wherein $R^1$ is $C_{1-3}$-alkyl or $C_{1-3}$ acyl and $R^2$ is H or $C_{1-3}$-alkyl.

Specific compounds of interest within Formula II are the following:

1β-Acetylthio-15β,16β-methylene-7α-methylthio-3-oxo-17α-pregn-4-ene-21,17-carbolactone; and 15β,16β-Methylene-1α,7α-dimethylthio-3-oxo-17α-pregn-4-ene-21,17-carbolactone.

Methods to make the compounds of Formula II are described in U.S. Pat. No. 4,789,668 to Nickisch et al which issued Dec. 6, 1988.

A third family of spirolactone-type compounds of interest is defined by a structure of Formula III:

(III)

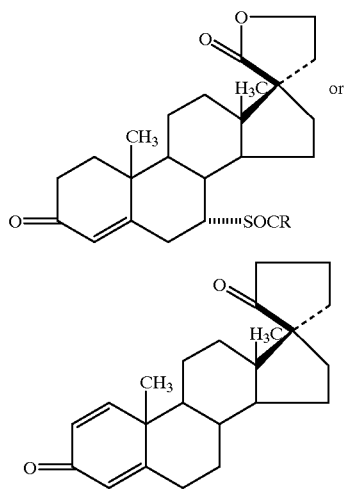

wherein R is lower alkyl, with preferred lower alkyl groups being methyl, ethyl, propyl and butyl. Specific compounds of interest include:

3β,21-dihydroxy-17α-pregna-5,15-diene-17-carboxylic acid γ-lactone;
3β,21-dihydroxy-17α-pregna-5,15-diene-17-carboxylic acid γ-lactone 3-acetate;
3β,21-dihydroxy-17α-pregn-5-ene-17-carboxylic acid γ-lactone;
3β,21-dihydroxy-17α-pregn-5-ene-17-carboxylic acid γ-lactone 3-acetate;
21-hydroxy-3-oxo-17α-pregn-4-ene-17-carboxylic acid γ-lactone;
21-hydroxy-3-oxo-17α-pregna-4,6-diene-17-carboxylic acid γ-lactone;
21-hydroxy-3-oxo-17α-pregna-1,4-diene-17-carboxylic acid γ-lactone;
7α-acylthio-21-hydroxy-3-oxo-17α-pregn-4-ene-17-carboxylic acid γ-lactones; and
7α-acetylthio-21-hydroxy-3-oxo-17α-pregn-4-ene-17-carboxylic acid γ-lactone.

Methods to make the compounds of Formula III are described in U.S. Pat. No. 3,257,390 to Patchett which issued Jun. 21, 1966.

A fourth family of compounds of interest is represented by Formula IV:

(IV)

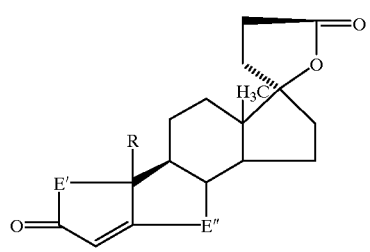

wherein E' is selected from the group consisting of ethylene, vinylene and (lower alkanoyl)thioethylene radicals, E" is selected from the group consisting of ethylene, vinylene, (lower alkanoyl)thioethylene and (lower alkanoyl) thiopropylene radicals; R is a methyl radical except when E' and E" are ethylene and (lower alkanoyl) thioethylene radicals, respectively, in which case R is selected from the group consisting of hydrogen and methyl radicals; and the selection of E' and E" is such that at least one (lower alkanoyl)thio radical is present.

A preferred family of compounds within Formula IV is represented by Formula V:

(V)

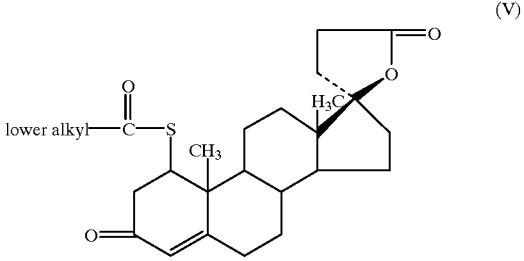

A more preferred compound of Formula V is 1-acetylthio-17α-(2-carboxyethyl)-17β-hydroxy-androst-4-en-3-one lactone.

Another preferred family of compounds within Formula IV is represented by Formula VI:

(VI)

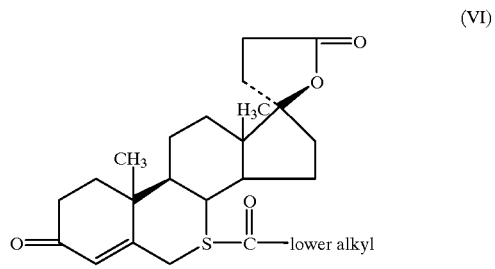

More preferred compounds within Formula VI include the following:

7α-acetylthio-17α-(2-carboxyethyl)-17β-hydroxy- androst-4-en-3-one lactone;
7β-acetylthio-17α-(2-carboxyethyl)-17β-hydroxy-androst-4-en-3-one lactone;
1α,7α-diacetylthio-17α-(2-carboxyethyl)-17β-hydroxy-androsta-4,6-dien-3-one lactone;
7α-acetylthio-17α-(2-carboxyethyl)-17β-hydroxy-androsta-1,4-dien-3-one lactone;
7α-acetylthio-17α-(2-carboxyethyl)-17β-hydroxy-19-norandrost-4-en-3-one lactone; and
7α-acetylthio-17α-(2-carboxyethyl)-17β-hydroxy-6α-methylandrost-4-en-3-one lactone;

In Formula IV–VI, the term "alkyl" is intended to embrace linear and branched alkyl radicals containing one to about eight carbons. The term "(lower alkanoyl)thio" embraces radicals of the formula lower alkyl

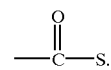

Of particular interest is the compound spironolactone having the following structure and formal name:

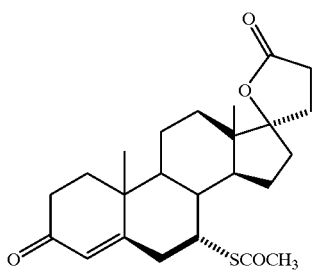

"spironolactone": 17-hydroxy-7α-mercapto-3-oxo-17α-pregn-4-ene-21-carboxylic acid γ-lactone acetate Methods to make compounds of Formula IV–VI are described in U.S. Pat. No. 3,013,012 to Cella et al which issued Dec. 12, 1961. Spironolactone is sold by G. D. Searle & Co., Skokie, Ill., under the trademark "ALDACTONE", in tablet dosage form at doses of 25 mg, 50 mg and 100 mg per tablet.

Another group of aldosterone antagonists of particular interest are epoxy steroidal aldosterone antagonist compounds having a steroidal nucleus substituted with an epoxy-type moiety. The term "epoxy-type" moiety is intended to embrace any moiety characterized in having an oxygen atom as a bridge between two carbon atoms, examples of which include the following moieties:

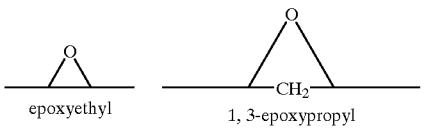

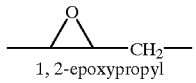

The term "steroidal", as used in the phrase "epoxy-steroidal", denotes a nucleus provided by a cyclopenteno-phenanthrene moiety, having the conventional "A", "B", "C" and "D" rings. The epoxy-type moiety may be attached to the cyclopentenophenanthrene nucleus at any attachable or substitutable positions, that is, fused to one of the rings of the steroidal nucleus or the moiety may be substituted on a ring member of the ring system. The phrase "epoxy-steroidal" is intended to embrace a steroidal nucleus having one or a plurality of epoxy-type moieties attached thereto.

Epoxy-steroidal aldosterone antagonists suitable for use in the present methods include a family of compounds having an epoxy moiety fused to the "C" ring of the steroidal nucleus. Especially preferred are 20-spiroxane compounds characterized by the presence of a 9α, 11α-substituted epoxy moiety. Compounds 1 through 11, below, are illustrative 9α,11α-epoxy-steroidal compounds that may be used in the present methods. These epoxy steroids may be prepared by procedures described in Grob et al., U.S. Pat. No. 4,559,332. Additional processes for the preparation of 9,11-epoxy steroidal compounds and their salts are disclosed in Ng et al., WO97/21720 and Ng et al., WO98/25948.

| Compound # | Structure | Name |
|---|---|---|
| 1 | 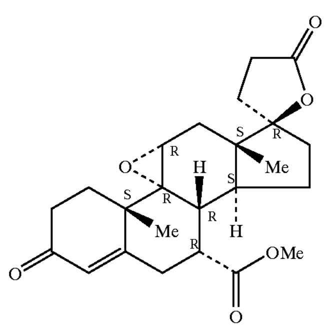 | Pregn-4-ene-7,21-dicarboxylic acid, 9,11-epoxy-17-hydroxy-3-oxo-, γ-lactone, methyl ester, (7α,11.α.,17α)- |
| 2 | 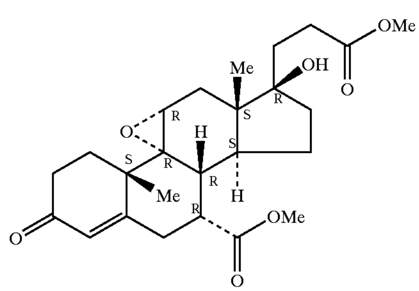 | Pregn-4-ene-7,21-dicarboxylic acid, 9,11-epoxy-17-hydroxy-3-oxo-dimethyl ester, (7α,11α,17α)- |

-continued

| Compound # | Structure | Name |
|---|---|---|
| 3 | 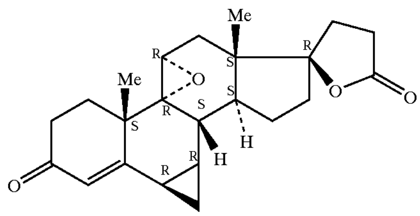 | 3'H-cyclopropa[6,7]pregna-4,6-diene-21-carboxylic acid, 9,11-epoxy-6,7-dihydro-17-hydroxy-3-oxo, γ-lactone, (6β,7β,11β,17β)- |
| 4 | 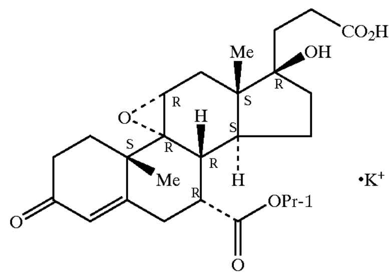 | Pregn-4-ene-7,21-dicarboxylic acid, 9,11-epoxy-17-hydroxy-3-oxo-, 7-(1-methylethyl) ester, monopotassium salt, (7a,11a,17a)- |
| 5 | 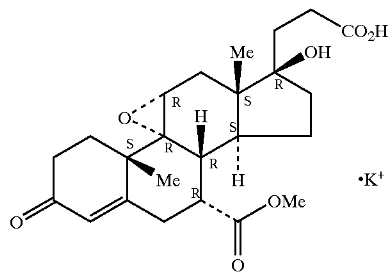 | Pregn-4-ene-7,21-dicarboxylic acid, 9,11-epoxy-17-hydroxy-3-oxo-, 7-methyl ester, monopotassium salt, (7a,11a,17a)- |
| 6 | 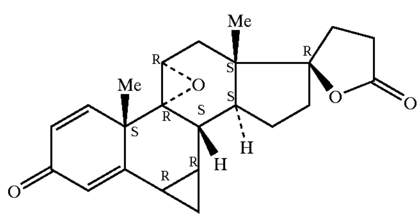 | 3'H-cyclopropa[6,7]pregna-1,4,6-triene-21-carboxylic acid, 9,11-epoxy-6,7-dihydro-17-hydroxy-3-oxo-, g-lactone(6a,7a,11.a)- |
| 7 | 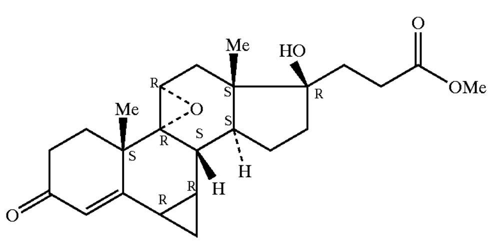 | 3'H-cyclopropa[6,7]pregna-4,6-diene-21-carboxylic acid, 9,11-epoxy-6,7-dihydro-17-hydroxy-3-oxo-, methyl ester, (6a,7a,11a,17a)- |
| 8 | 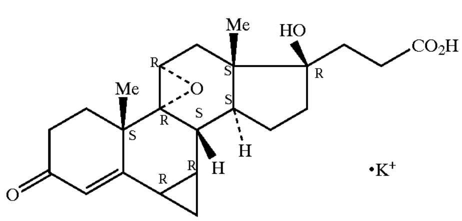 | 3'H-cyclopropa[6,7]pregna-4,6-diene-21-carboxylic acid, 9,11-epoxy-6,7-dihydroxy-17-hydroxy-3-oxo-, monopotassium salt, (6a,7a,11a,17a)- |

-continued

| Compound # | Structure | Name |
|---|---|---|
| 9 | 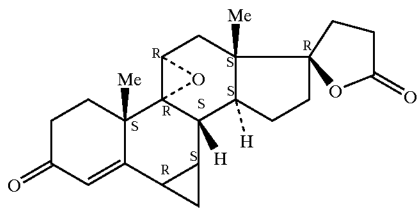 | 3'H-cyclopropa[6,7]pregna-4,6-diene-21-carboxylic acid, 9,11-epoxy-6,7-dihydro-17-hydroxy-3-oxo, g-lactone, (6a,7a,11a.,17a)- |
| 10 | 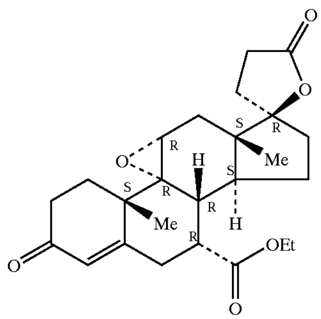 | Pregn-4-ene-7,21-dicarboxylic acid, 9,11-epoxy-17-hydroxy-3-oxo, g-lactone, ethyl ester, (7a,11a,17a)- |
| 11 | 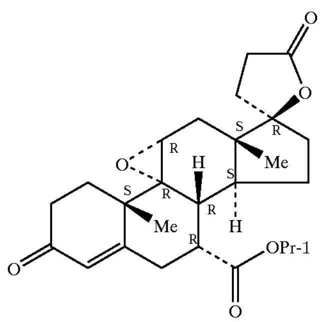 | Pregn-4-ene-7,21-dicarboxylic acid, 9,11-epoxy-17-hydroxy-3-oxo-, g-lactone, 1-methylethyl ester, (7a,11a,17a)- |

Of particular interest is the compound eplerenone which is compound 1 as shown above. Eplerenone is an aldosterone receptor antagonist and has a higher specificity for aldosterone receptors than spironolactone. Selection of eplerenone as the aldosterone antagonist in the present combination therapy likewise should be beneficial, yet diminish certain side effects such as gynecomastia.

A diuretic agent may be used with the combination of ACE inhibitor and aldosterone antagonist. Such diuretic agent may be selected from several known classes, such as thiazides and related sulfonamides, potassium-sparing diuretics, loop diuretics and organic mercurial diuretics. The term diuretic is not intended to embrace spirolactone-type compounds.

Examples of thiazides are bendroflumethiazide, benzthiazide, chlorothiazide, cyclothiazide, hydrochlorotthiazide, hydroflumethiazode, methyclothiazide, polythiazide and trichlormethiazide.

Examples of related sulfonamides are chlorthalidone, quinethazone and metolazone.

An example of a non-thiazide sulfonamide diuretic is metolazone.

Examples of potassium-sparing diuretics are triameterene and amiloride.

Examples of loop diuretics, i.e., diuretics acting in the ascending limb of the loop of Henle of the kidney, are furosemide and ethynacrylic acid.

Examples of organic mercurial diuretics are mercaptomerin sodium, merethoxylline procaine and mersalyl with theophylline.

Biological Evaluation

Human Clinical Trials

A combination therapies comprising two or more of the agents or compounds selected from the group consisting of ACE inhibitors, spironolactone, digoxin, and loop diuretics was evaluated in humans as described in the following clinical trials. The use of the term "placebo" is intended to embrace therapy which includes cardiovascular treatments described herein in the absence of spironolactone.

Patients

One thousand six hundred and sixty-three (1,663) patients with severe heart failure were enrolled in the study. Patients were eligible for enrollment in the study if they had a history of New York Heart Association (NYHA) Class IV heart failure within 6 months but no less than 6 weeks from randomization, and were NYHA Class III or IV at the time of enrollment. Eligible patients had a left ventricular ejection fraction of $\leq 35$ percent and were to be receiving treatment with an angiotensin-converting enzyme inhibitor, if tolerated, and a loop diuretic. Treatment with digitalis and vasodilators was allowed, but potassium-sparing diuretics were not permitted. Oral potassium supplements were not recommended unless hypokalemia (serum potassium <3.5 mmol per liter) developed. A low salt diet (100–200 mEg/day, sodium) was recommended to all patients. Patients were excluded from the trial if they had clinically significant operable valvular disease (other than mitral or tricuspid regurgitation), congenital heart disease, unstable angina, primary hepatic failure, active malignancy, a heart transplant or were a candidate for heart transplantation, or any life threatening diseae (other than heart failure). Other criteria for exclusion were a serum creatinine concentration >2.5 mg per deciliter (>220 μmol per liter) or a serum potassium concentration >5.0 mmol per liter. The protocol was approved by the Institutional Review Boards or Ethics Committees of all participating institutions. Written informed consent was obtained from all patients.

Study Design

After the initial evaluation, patients were randomly assigned in a double-blind fashion to receive either oral spironolactone (Aldactone®, Searle) 25 mg once daily or matching placebo, in addition to their usual medication(s). After 8 weeks of treatment, at the discretion of the investigator, study drug could be increased to 50 mg once daily if there were signs and/or symptoms of progression of heart failure without evidence of hyperkalemia. If at any time the patient developed hyperkalemia, the dose could be decreased to 25 mg every other day; however, the investigator was encouraged to first adjust concomitant medications. Follow-up evaluations were conducted every 4 weeks until Week 12, and then every 3 months thereafter until study completion. Clinicial laboratory determinations, including serum potassium, creatinine, sodium and N-terminal pro-atrial natriuretic peptide, were performed at baseline at Weeks 1, 4, 5, 8, 12 and then every 3 months thereafter until study completion. For patients in whom the study drug was increased to 50 mg once daily, a serum potassium determination was also performed at Week 9. Study medication could be withheld for serious hyperkalemia (potassium >6.0 mmol per liter), serum creatinine >4.0 mg per deciliter (354 μmol per liter), intercurrent illness, or any conditions deemed medically necessary to protect the patient's best interest. However, all parties remained in the study to track hospitalizations and deaths.

A health-related quality of life questionnaire was also completed by patients at various intervals during the trial.

An independent Data and Safety Monitoring Board met periodically to review the unblinded results and an events committee adjudicated the cause of death and hospitalizations in a blinded fashion.

End Points

The primary end point of the study was total all-cause mortality. Secondary end points included cardiac mortality, incidence of cardiac hospitalization, the combined incidence of cardiac mortality plus hospitalization, and changes in NYHA class. The effect of spironolactone was also assessed in subgroups of patients defined on the basis of the following six pre-randomization variables: ejection fraction, etiology of heart failure, serum creatinine concentration, age, angiotensin-converting enzyme inhibitor type and dose, and digitalis use.

Statistical Analysis

Analysis of all-cause mortality (the primary end point) included all patients randomized, according to the randomly assigned treatment group based on the intention-to-treat principle. Kaplan-Meier methods were used to construct cumulative survival curves for the two treatment groups. The primary comparison between the two groups was based on a log-rank test; Cox prbportional-hazards regression models were developed to explore the effects of baseline variables on the estimated effect of spironolactone. Formal assessment of efficacy in this trial used a group sequential monitoring plan with a Lan-DeMets alpha-spending approach and an O'Brien-Fleming spending function.

The sample size was calculated (using a method developed by Lakatos) on the basis of the following assumptions: annual mortality rate in the placebo group would be 38 percent; the risk of death by would be reduced by 17 percent in the spironolactone group; and approximately 5 percent of the participants in the spironolactone group would stop study medication each year. The power to detect a difference between treatment groups under these assumptions was set at 90 percent (alpha-level of 0.05 by a two-tailed test).

The Data Safety Monitoring Board reviewed the accruing data from this trial for evidence of efficacy and safety, and at each meeting calculated the projected cumulative Type I error spent for efficacy. Since two large trials in heart failure had shown decidedly non-exponential distributions of time to death, the computations for group sequential monitoring of all-cause mortality were based on life-table calculations to project event rates. The critical z-value for declaring statistically significant efficacy of treatment planned at the end of the trial was 2.02, corresponding to a p-value of 0.043.

Recruitment

In total, 1,663 patients were enrolled from 195 centers in 15 countries.

Patient Characteristics

Patient demographic, vital signs, and cardiac status at baseline are summarized in Table 1A and Table 1B. Data presented in Table 1B have been audited, updated, and revised relative to Table 1A.

In total, 1,633 patients from 195 centers (15 countries) were enrolled in the trial; 841 were randomized to placebo and 822 to spironolactone. As shown in Table 1A and 1B, the baseline characteristics were similar for patients randomized to placebo and spironolactone. There were 8 patients (3 placebo, 5 spironolactone) that had history of NYHA Class IV, but were not Class III or IV at the time of randomization. Reasons for discontinuation of study medication are shown in Table 2A. During the trial, 17 patients were withdrawn from study medication due to cardiac transplantation, 7 in the spironolactone group and 10 in the placebo group; one patient from the placebo group died 4 days after cardiac transplantation. Patients who discontinued study medication were followed by regularly scheduled follow-up telephone contact for determination of vital status. After a mean follow-up of 24 months, the average dose of study medication was 32.12 mg for placebo and 26.75 mg for spironolactone.

TABLE 1A

Baseline Characteristics

| Characteristics | Placebo (n = 841) | Spironolactone (n = 822) | Total (n = 1663) |
|---|---|---|---|
| Age(yr) | 65.1 ± 12 | 65.2 ± 12.1 | 65.1 ± 12 |
| Race | | | |
| Caucasian | 86% | 87% | 87% |
| Sex | | | |
| Male | 614(73%) | 603(73%) | 1217(73%) |
| Female | 227(27%) | 219(27%) | 446(27%) |
| Blood Pressure (mm Hg) | | | |
| Systolic | 122 ± 20 | 123 ± 21 | 122 ± 20 |
| Diastolic | 75 ± 11 | 75 ± 12 | 75 ± 12 |

TABLE 1A-continued

Baseline Characteristics

| Characteristics | Placebo (n = 841) | Spironolactone (n = 822) | Total (n = 1663) |
|---|---|---|---|
| Heart Rate (beats/min) | 81.1 ± 14.8 | 81 ± 14 | 81 ± 14 |
| New York Heart Association Class | | | |
| II | 3(0%) | 5(1%) | 8(0%) |
| III | 581(69%) | 591(72%) | 1172(70%) |
| IV | 257(31%) | 226(27%) | 483(29%) |
| Left Ventricular | | | |
| Ejection Fraction(%) | 25.2 ± 6.8 | 25.6 ± 6.7 | 25.4 ± 6.7 |
| Cause of Heart Failure | | | |
| Ischemic | 453(54%) | 454(55%) | 907(55%) |
| Non-ischemic | 386(46%) | 368(45%) | 754(45%) |
| Medication(% of Patients) | | | |
| Loop Diuretic | 94% | 99% | 96% |
| ACE Inhibitor | 88% | 89% | 89% |
| Digitalis | 71% | 73% | 72% |
| Aspirin | 38% | 33% | 35% |
| Potassium Supplements | 24% | 25% | 25% |
| Beta Blockers | 7% | 7% | 7% |
| Dose of ACE-Inhibitor (mg/day) | | | |
| Dose of Captopril | 62.1 | 63.4 | 62.7 |
| Dose of Enalapril | 16.5 | 13.5 | 15.0 |
| Dose of Lisinopril | 13.1 | 15.5 | 14.4 |

TABLE 1B

BASE-LINE CHARACTERISTICS OF THE PATIENTS

| CHARACTERISTIC | PLACEBO GROUP (N = 841) | SPIRONOLACTONE GROUP (N = 822) |
|---|---|---|
| Age - yr | 65 ± 12 | 65 ± 12 |
| White race - % | 86 | 87 |
| Sex - no. (%) | | |
| Male | 614 (73) | 603 (73) |
| Female | 227 (27) | 219 (27) |
| Blood pressure - mm Hg | | |
| Systolic | 123 ± 30 | 123 ± 31 |
| Diastolic | 75 ± 11 | 75 ± 12 |
| Heart rate - beats/min | 81 ± 15 | 81 ± 14 |
| New York Heart Association class - no.(%) | | |
| II | 3 (0.4) | 4 (0.5) |
| III | 581 (69) | 592 (72) |
| IV | 257 (31) | 226 (27) |
| Left ventricular ejection fraction - %† | 25.2 ± 6.8 | 25.6 ± 6.7 |
| Cause of heart failure - no.(%)‡ | | |
| Ischemic | 455 (54) | 454 (55) |
| Nonischemic | 386 (46) | 368 (45) |
| Medications - % | | |
| Loop diuretics | 100 | 100 |
| ACE inhibitors | 94 | 95 |
| Digitalis | 72 | 75 |
| Aspirin | 37 | 36 |
| Potassium supplements | 27 | 29 |
| Beta-blockers | 10 | 11 |
| Mean dose of ACE inhibitors - mg/day | | |
| Captopril | 62.1 | 63.4 |
| Enalapril | 16.5 | 13.5 |
| Lisinopril | 13.1 | 15.5 |

*Plus-minus values are means ± SD. ACE denotes angiotensin-converting enzyme.
†The ejection fraction could be measured by contrast ventriculography, gated radionuclide ventriculography, or echocardiography.
‡The cause of heart failure was determined on the basis of a patient's history, angiographic evidence, or both. Data on the cause of heart failure were not available for two patients in the placebo group.

TABLE 2A

Treatment Discontinuation

| | Placebo | Spironolactone |
|---|---|---|
| Patients Enrolled | 841 | 822 |
| Death | 351 (42%) | 269 (33%) |
| Discontinued Therapy During Study | 137 (16%) | 134 (16%) |
| Treatment Failure | 25 (3%) | 9 (1%) |
| Adverse Effects | 29 (3%) | 51 (6%) |
| Heart Transplants | 10 (1%) | 7 (1%) |
| Non-Compliance/Physician's Choice | 75 (9%) | 67 (8%) |

Effect of Spironolactone on Survival (See FIG. 1A, FIG 1B, and FIG. 2)

Among the 1,663 patients randomized, there were 351 deaths (41.7 percent) in the placebo group and 269 deaths (32.7 percent) in the spironolactone group; this difference represents an estimated 26 percent decrease in the risk of death by Cox proportional-hazards model (95 percent confidence interval, 13 to 37 percent; p<0.00001) in patients randomized to spironolactone (FIGS. 1A and 1B). Data presented in FIG. 1B have been audited, updated, and revised relative to FIG. 1A. Preliminary analysis based upon investigator initiated (unadjudicated) case report forms suggests that the reduction in mortality observed with spironolactone was due to decreases in both progressive heart failure and sudden death.

Figure 4:
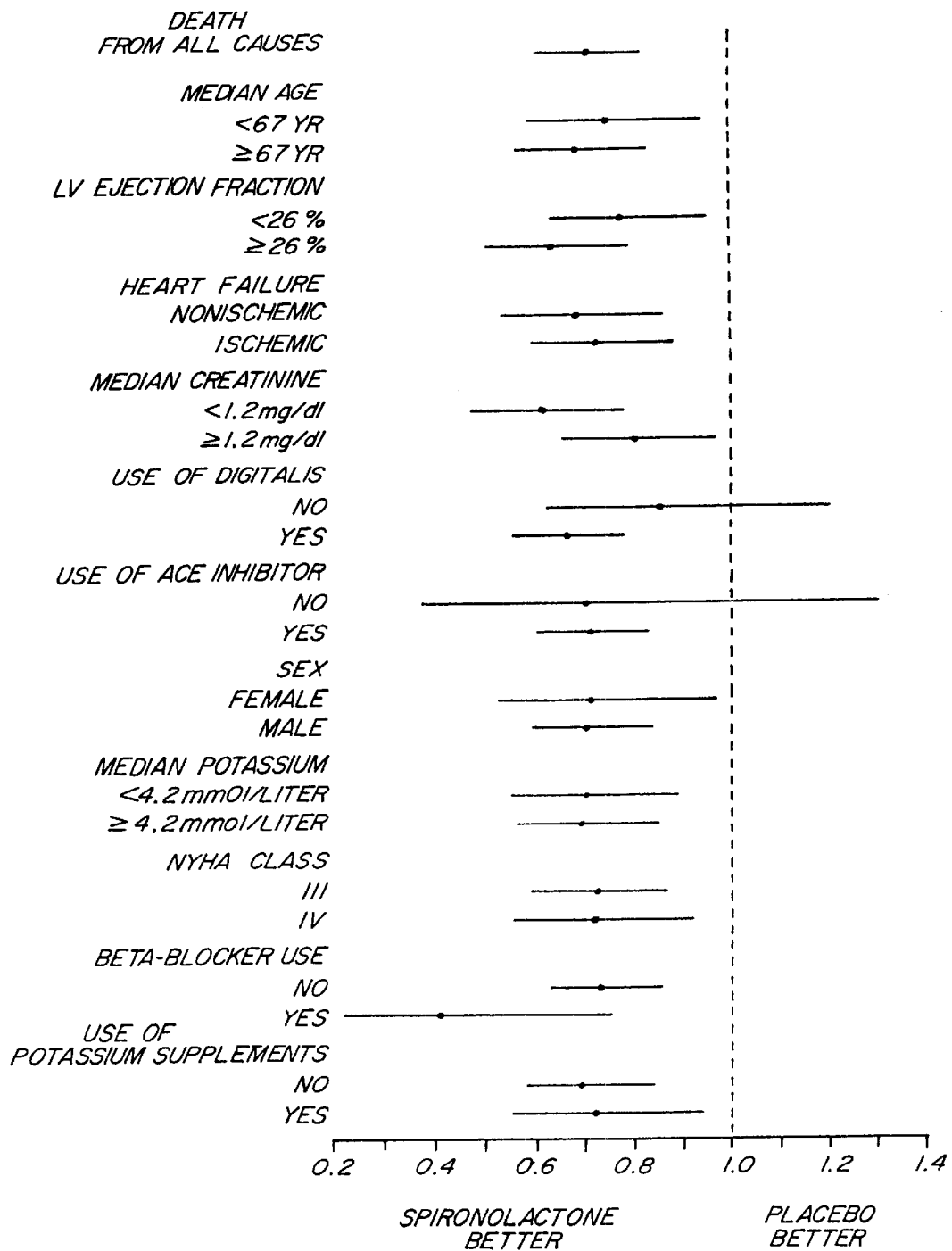
FIG. 4 shows relative risks of death from all causes and according to demographic and clinical characteristics.
Figure 5:
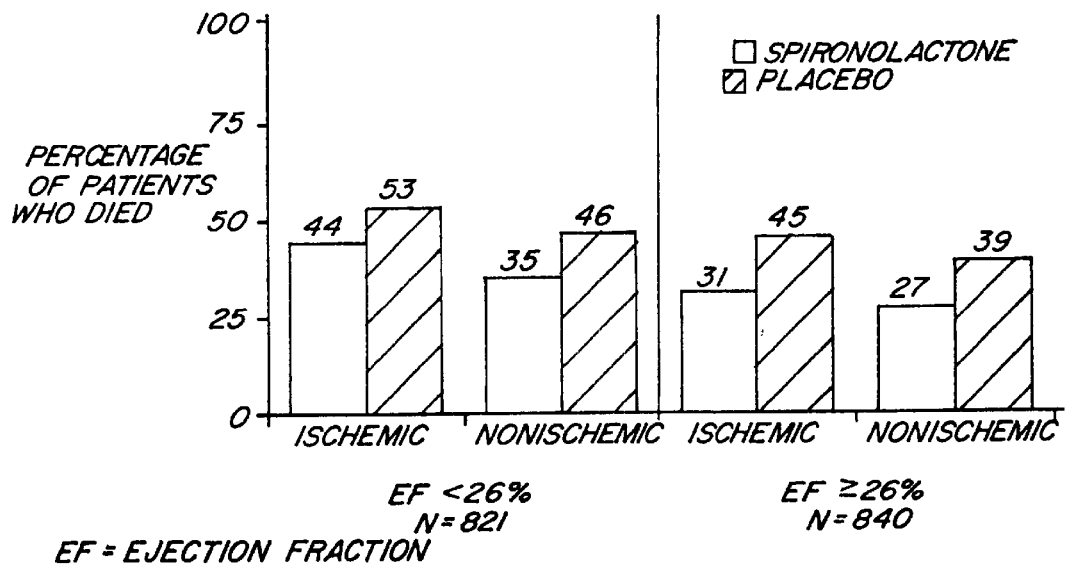
FIG. 5 shows the percentage of deaths according to baseline heart failure etiology, subclassified by ejection fraction.

Data after careful audit and update were revised as shown in FIG. 1B, Table 2B, FIG. 4, and Table 2C. There were 386 deaths in the placebo group (46 percent) and 284 deaths in the spironolactone group (35 percent), representing a 30 percent reduction in the risk of death (relative risk of death among the patients in the spironolactone group, 0.70 by a Cox proportional-hazards model; 95 percent confidence interval, 0.60 to 0.82; P<0.001). A total of 314 deaths in the placebo group (37 percent) and 226 deaths in the spironolactone group (27 percent) were attributed to cardiac causes, representing a 31 percent reduction in the risk of death from cardiac causes (relative risk, 0.69; 95 percent confidence interval, 0.58 to 0.82; P<0.001). The reduction in the risk of death among the patients in the spironolactone group was attributed to significantly lower risks of both death from progressive heart failure and sudden death from cardiac causes.

The reduction in the risk of death among patients in the spironolactone group was analyzed in each of six prespecified subgroups as well as in retrospective analyses performed according to sex, NYHA class, base-line serum potassium concentration, use of potassium supplements, and use of beta-blockers. FIG. 4, Table 2C, FIG. 5–9. The estimated beneficial effect was similar across geographic regions.

During the trial, 336 patients in the placebo group and 260 patients in the spironolactone group were hospitalized at least once for cardiac reasons (Table 2B). In total, there were 753 hospitalizations for cardiac causes in the placebo group and 515 in the spironolactone group, representing a 30 percent reduction in the risk of hospitalization for cardiac causes among patients in the spironolactone group (relative risk, 0.70; 95 percent confidence interval, 0.59 to 0.82; P<0.001)(Table 2B). Analysis of the combined end point of death from cardiac causes or hospitalization for cardiac causes revealed a 32 percent reduction in the risk of this end point among patients in the spironolactone group as compared with those in the placebo group (relative risk, 0.68; 95 percent confidence interval, 0.59 to 0.78; P<0.001) (Table 2C).

The reduction in mortality in patients randomized to spironolactone was demonstrated regardless of age, sex, etiology of heart failure, NYHA functional class III or IV, digitalis use, baseline serum potassium or creatinine levels. There was a trend toward a greater reduction in mortality in spironolactone-treated patients with baseline ejection fractions $\geq 27$ (FIGS. 4–10).

Figure 3:
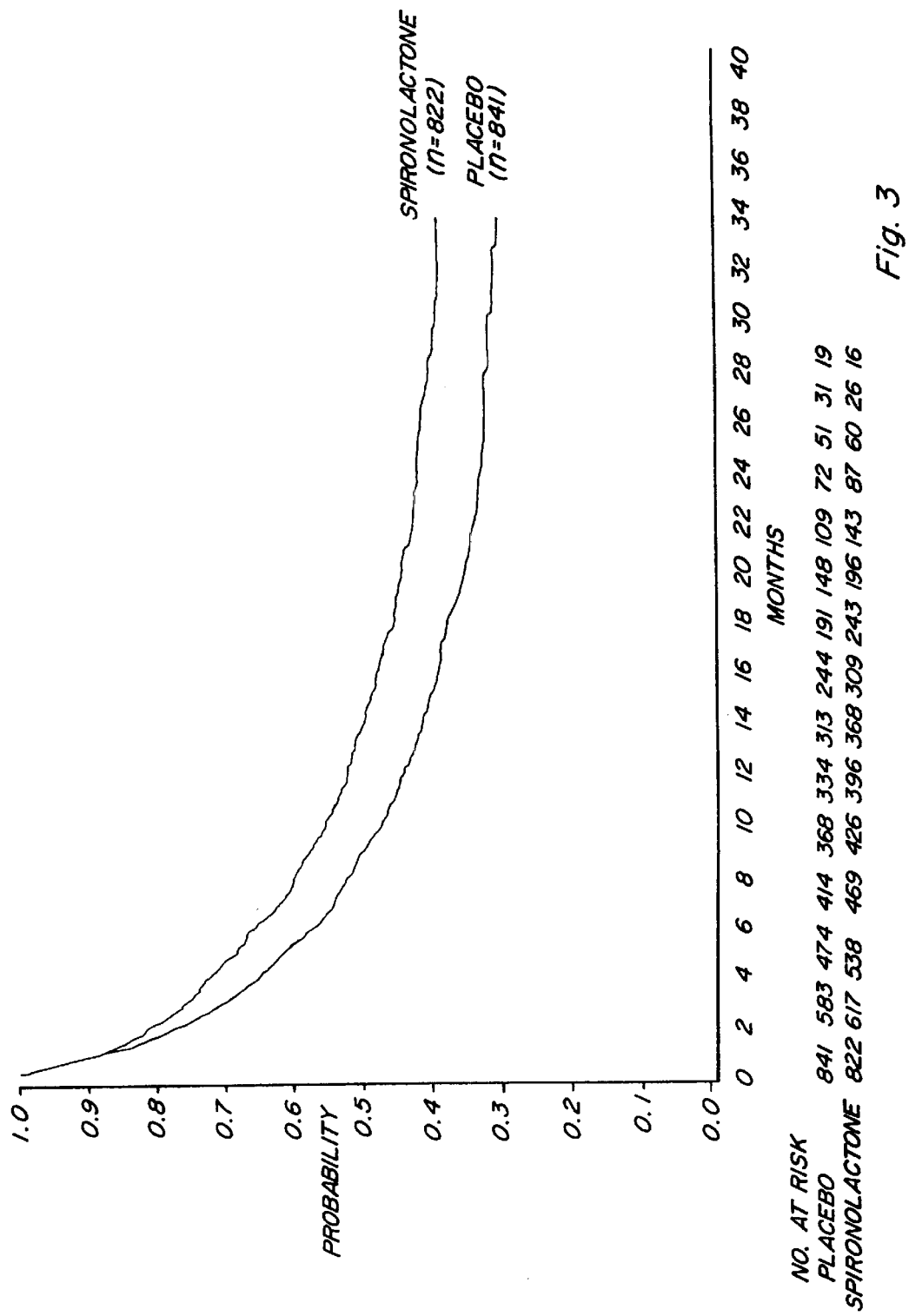
FIG. 3 shows a Kaplan-Meier analysis of combined end-point of non-fatal hospitalization plus total mortality in placebo and spironolactone treated groups. Both groups were co-administered stable doses of an ACE inhibitor and a loop diuretic.

Effect of Spironolactone on Non-Fatal Hospitalizations (See FIG. 3)

During the trial, 510 (61 percent) placebo-treated and 445 (54 percent) spironolactone-treated patients had at least one non-fatal hospitalization, representing 1,595 hospitalizations for the placebo group and 1,347 hospitalizations for the spironolactone group. Using the Cox proportional-hazards model for the combined end point analysis of total non-fatal hospitalization and total all-cause mortality, we observed a 20 percent risk reduction in the spironolactone group compared to the placebo group (95 percent confidence interval of 10 to 29 percent, p=0.00017) (FIG. 3).

TABLE 2C

RELATIVE RISKS OF THE COMBINED END POINTS OF DEATH OR HOSPITALIZATION IN THE SPIRONOLACTONE GROUP

| END POINT | RELATIVE RISK (95% CI) | P VALUE |
|---|---|---|
| Death from cardiac causes or hospitalization for cardiac causes | 0.68(0.59–0.78) | <0.001 |
| Death from any cause or hospitalization for any reason | 0.77(0.68–0.86) | <0.001 |
| Death from any cause or hospitalization for cardiac causes | 0.68(0.60–0.77) | <0.001 |

Effect of Spironolactone on Changes of NYHA Functional Class: (See Table 3)

Three categories were used to assess changes in the symptoms of heart failure: improvement, no change, and worsening or death. The condition of patients who were in NYHA class III at base line was considered to have improved if they were in NYHA class I or II at the end of the study and considered to have worsened if they were in NYHA class IV (or had died). The condition of patients who were in NYHA class IV at base line was considered to have improved if they were in NYHA class I, II, or III at the end of the study; other patients in NYHA class IV at base line either had no change at the end of the study or died. Using the Cochran-Mantel-Haenszl test for association between drug therapy and NYHA class outcome (worse, same, improvement), there was a significant improvement from the baseline NYHA functional class in the spironolactone group compared to the placebo group (p=0.001). In the placebo group, the condition of 33 percent of the patients improved; it did not change in 18 percent, and it worsened in 48 percent. In the spironolactone group, the condition of 41

TABLE 2B

RELATIVE RISKS OF DEATH AND HOSPITALIZATION

Figure 6:
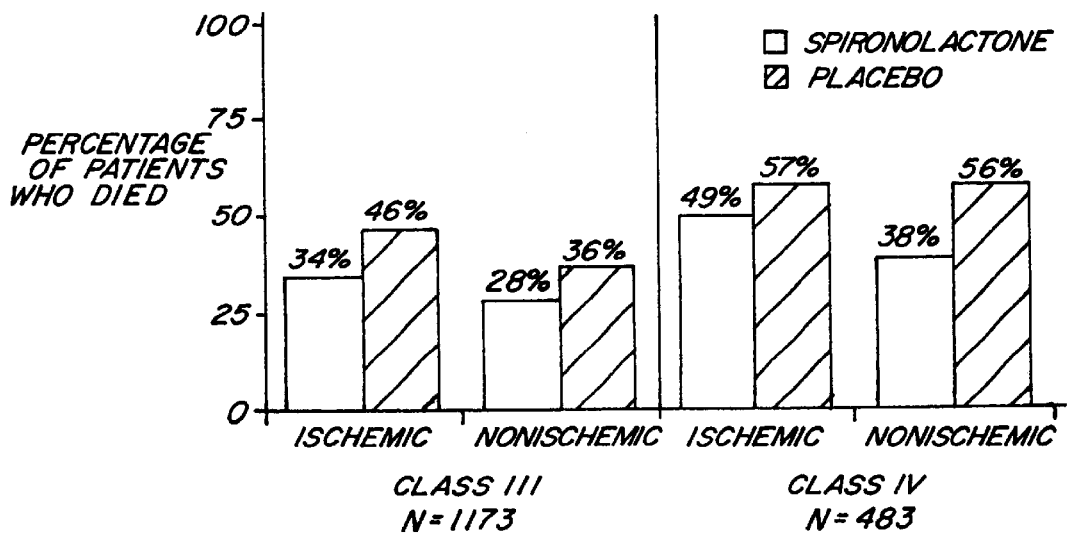
FIG. 6 shows the percentage of deaths according to to baseline heart failure etiology, subclassified by New York Heart Association Class.
Figure 7:
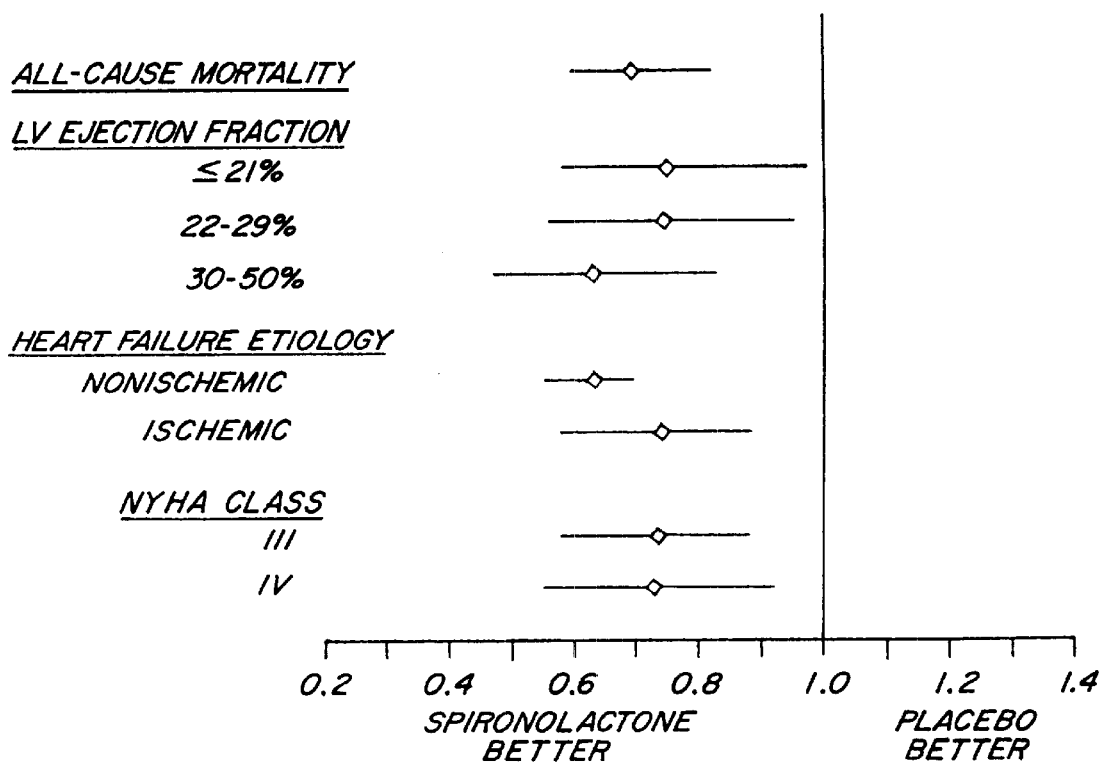
FIG. 7 shows relative risk of death from all causes according to baseline characteristics.
Figure 8:
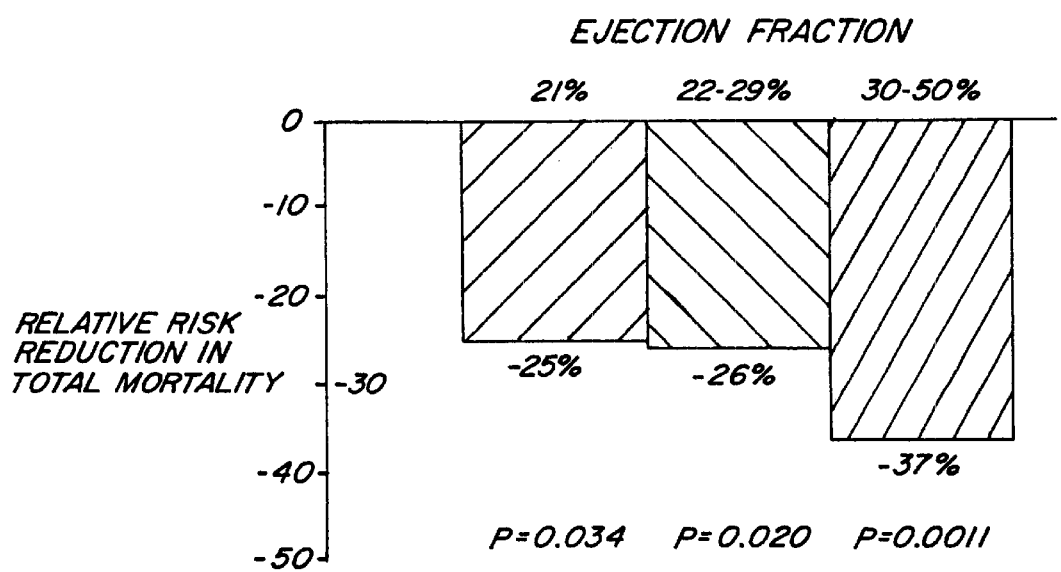
FIG. 8 Shows risk reduction by ejection fraction tertiles for spironolactone relative to placebo.
Figure 9:
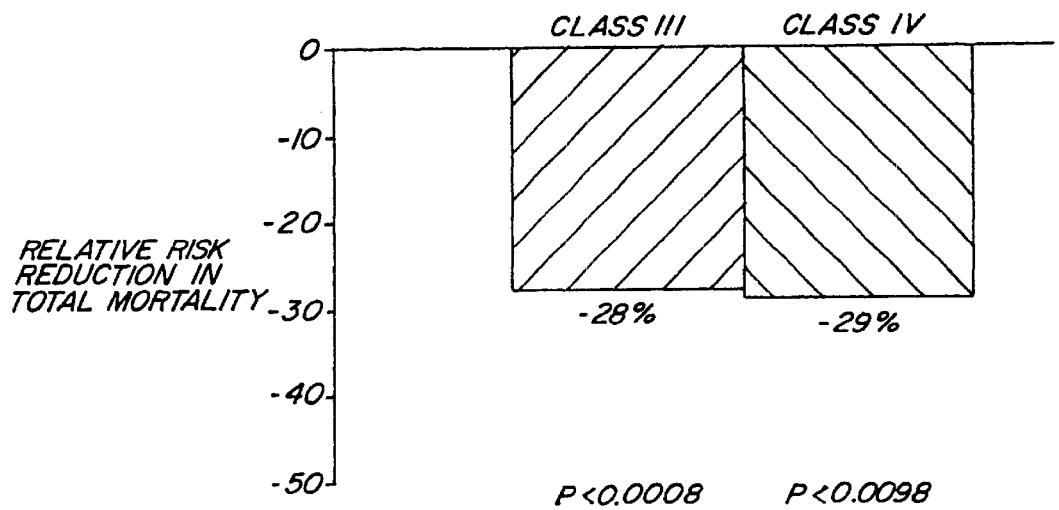
FIG. 9 shows mortality rates according to baseline New York Heart Association Class for spironolactone relative to placebo.
Figure 10:
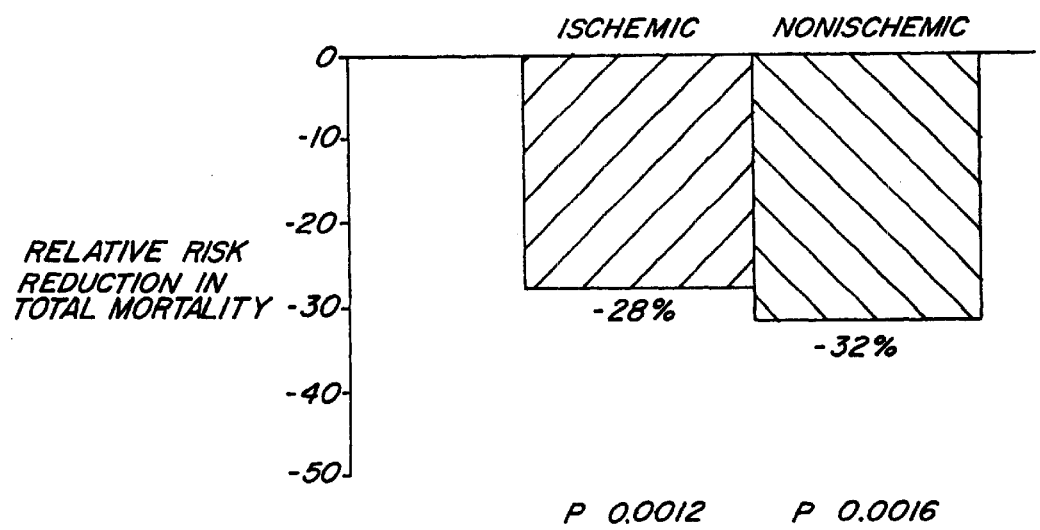
FIG. 10 shows mortality rates according to baseline heart failure etiology for spironolactone relative to placebo.

| VARIABLE | PLACEBO GROUP (N = 841) | SPIRONOLACTONE GROUP (N = 822) | RELATIVE RISK (95% CI)* | P VALUE |
|---|---|---|---|---|
| | no. of patients | | | |
| Cause of death | | | | |
| Cardiac causes | 314 | 226 | 0.69(0.53–0.82) | <0.001 |
| Progression of hear failure† | 189 | 127 | 0.64(0.51–0.80) | <0.002 |
| Sudden death‡ | 110 | 82 | 0.71(0.54–0.95) | 0.02 |
| Myocardial infraction | 15 | 17 | | |
| Other cardiovascular causes | 13 | 12 | | |
| Stroke | 11 | 8 | | |
| Noncardiovascular causes | 41 | 29 | | |
| Unknown | 7 | 9 | | |
| Total | 386 | 284 | 0.70(0.60–0.82) | <0.001 |
| | no. of patients/no. of events | | | |
| Reason for hospitalization | | | | |
| Cardiac causes§ | 336/753 | 260/515 | 0.70(0.59–0.82) | <0.001 |
| Worsening heart failure | 300/663 | 215/413 | 0.65(0.54–0.77) | <0.001 |
| Angina | 35/44 | 43/66 | | |
| Ventricular arrhythmias | 24/31 | 23/25 | | |
| Myocardial infraction | 14/15 | 10/11 | | |
| Other cardiovascular causes | 112/163 | 117/169 | | |
| Stroke | 20/24 | 14/15 | | |
| Noncardiovascular causes | 232/377 | 223/361 | | | percent of the patients improved; it did not change in 21 percent, and it worsened in 38 percent. The difference between groups was significant (P<0.001 by the Wilcoxon test). As shown in FIGS. 6, 7, and 9, spironolactone co-therapy resulted in a total reduction in mortality in patients who were classified as Class III and Class IV upon entry to this study.

TABLE 3

NYHA Class Changes

|  | Placebo | Aldactone |
|---|---|---|
| Class III | (n = 581) | (n = 591) |
| Worse (Class IV + Death) | 227 (39%) | 189 (32%) |
| No Change | 176 (30%) | 186 (31%) |
| Improvement | 178 (31%) | 216 (37%) |
| Class IV | (n = 257) | (n = 226) |

TABLE 3-continued

NYHA Class Changes

|  | Placebo | Aldactone |
|---|---|---|
| Death | 134 (52%) | 96 (42%) |
| No Change | 31 (12%) | 26 (12%) |
| Improvement | 92 (36%) | 104 (46%) |

Safety

Changes in serum potassium, serum creatinine, blood pressure, and heart rate are shown in Table 4. There were no significant differences between the two groups in serum sodium concentration, blood pressure, or heart rate during the study. The median creatinine and potassium concentrations did not change in the placebo group during the first year of follow-up, the period for which the data were most complete. During the same period, however, the median creatinine concentration in the spironolactone group increased by approximately 0.05 to 0.10 mg per deciliter (4 to 9 μmol per liter) and the median potassium concentration increased by 0.30 mmol per liter. The differences between the two groups were significant (P<0.001) but were not clinically important. The most frequent adverse reactions are listed in Table 5A. Gynecomastia and breast pain In males was reported in 9 patients (1.5 percent) in the placebo group compared to 51 patients (8.5 percent) in the spironolactone group, (p<0.0001). Serious hyperkalemia occurred in 10 patients (1.2 percent) in the placebo group compared to 14 patients (1.7 percent) in the spironolactone group. One patient discontinued therapy due to hypotension in the placebo group, and none in the spironolactone group.

Data presented in Table 5B have been audited, updated, and revised relative to Table 5A. Table 5B shows that serious hyperkalemia occurred in 10 patients in the placebo group (1 percent) and 14 patients in the spironolactone group (2 percent, P=0.42). Gynecomastia or breast pain was reported by 10 percent of the men in the spironolactone group and 1 percent of the men in the placebo group (P<0.001), causing more patients in the spironolactone group than in the placebo group to discontinue treatment (10 vs. 1, P=0.006).

TABLE 4

Changes in Serum Potassium and Creatinine, Blood Pressure and Heart Rate

|  | Baseline | Wk 4 | Wk 8 | Wk 12 | Mth 6 | Mth 9 | Mth 12 | Mth 18 | Mth 24 |
|---|---|---|---|---|---|---|---|---|---|
| Serum Potassium (mmol/Lt.) | | | | | | | | | |
| Placebo | 4.24 | 4.28 | 4.25 | 4.25 | 4.26 | 4.28 | 4.28 | 4.22 | 4.34 |
| Spiro | 4.21 | 4.54 | 4.53 | 4.58 | 4.56 | 4.54 | 4.52 | 4.59 | 4.52 |
| Serum Creatinine (mmol/Lt.) | | | | | | | | | |
| Placebo | 110 | 110 | 110 | 109 | 111 | 111 | 111 | 111 | 110 |
| Spiro | 109 | 115 | 114 | 116 | 116 | 117 | 115 | 113 | 113 |
| Heart Rate (beats/minute) | | | | | | | | | |
| Placebo | 81 | 81 | 80 | 80 | 78 | 79 | 77 | 78 | 78 |
| Spiro | 81 | 80 | 79 | 79 | 78 | 78 | 78 | 78 | 78 |
| Systolic Blood Pressure (mm/Hg) | | | | | | | | | |
| Placebo | 122 | 122 | 123 | 124 | 125 | 125 | 126 | 125 | 124 |
| Spiro | 123 | 121 | 122 | 121 | 123 | 124 | 123 | 125 | 122 |
| Diastolic Blood Pressure (mm/Hg) | | | | | | | | | |
| Placebo | 75 | 75 | 75 | 75 | 75 | 75 | 75 | 74 | 73 |
| Spiro | 75 | 74 | 73 | 73 | 74 | 74 | 74 | 74 | 77 |

TABLE 5A

Most Frequent Adverse Reactions

|  | No. of Patients (%) | |
|---|---|---|
| Adverse Reaction | Placebo (n = 841) | Aldactone (n = 822) |
| Patients with one or more events | 677 (80) | 649 (79) |
| Patients with no adverse events | 164 (20) | 173 (21) |
| Cardiovascular disorder | 375 (45) | 344 (42) |
| Progression Heart Failure | 167 (20) | 134 (16) |
| Angina | 84 (10) | 91 (11) |
| Palpitation | 33 (4) | 35 (4) |
| Respiratory Disorder | 386 (46) | 340 (41) |
| Dyspnea | 231 (27) | 194 (24) |
| Cough | 105 (12) | 96 (12) |
| Upper respiratory infection | 108 (13) | 114 (14) |
| Pneumonia | 18 (2) | 10 (1) |
| Pulmonary edema | 33 (4) | 23 (3) |
| Neoplasm | 4 (<1) | 4 (<1) |
| Urinary system disorder | 71 (8) | 75 (9) |

TABLE 5A-continued

Most Frequent Adverse Reactions

| | No. of Patients (%) | |
|---|---|---|
| Adverse Reaction | Placebo (n = 841) | Aldactone (n = 822) |
| Skin and appendages disorder | 69 (8) | 64 (8) |
| Musculoskeletal disorder | 104 (12) | 96 (12) |
| Nervous system disorder | 156 (19) | 175 (21) |
| Psychiatric disorder | 113 (13) | 110 (13) |
| Gastrointestinal disorder | 208 (25) | 210 (26) |
| Endocrine disorder | 20 (2) | 65 (8) |
| Gynecomastia (male) | 8 (1) | 43 (7)* |
| Breast pain (male) | 1 (<1) | 8 (1) |
| Edema | 56 (7) | 49 (6) |
| Serious hyperkalemia | 10 (1.2) | 14 (1.7) |
| Discontinuation due to hypertension | 56 (7) | 0 (0) |

*p < 0.0001

TABLE 5B

ADVERSE EVENTS

| | no. of patients (%) | |
|---|---|---|
| ADVERSE EVENT | PLACEBO GROUP (N = 841) | SPIRONOLACTONE GROUP (N = 822) |
| One or more events | 667 (79) | 674 (82) |
| Discontinuation because of adverse event | 40 (5) | 62 (8) |
| Cardiovascular disorders | 251 (30) | 248 (30) |
| Angina | 83 (10) | 103 (13) |
| Heart failure | 80 (10) | 52 (6) |
| Respiratory tract disorders | 285 (34) | 262 (32) |
| Cough | 117 (14) | 103 (13) |
| Dyspnea | 39 (5) | 34 (4) |
| Pneumonia | 25 (3) | 17 (2) |
| Pulmonary edema | 7 (0.8) | 5 (0.6) |
| Pleural effusion | 11 (1) | 3 (0.4) |
| Metabolic and nutritional disorders | 215 (26) | 269 (33) |
| Hyperuricemia | 25 (3) | 16 (2) |
| Neoplasm | 10 (1) | 13 (2) |
| Urinary system disorders | 89 (11) | 99 (12) |
| Disorders of skin and appendages | 72 (9) | 73 (9) |
| Musculosketal disorders | 118 (14) | 101 (12) |
| Nervous system disorders | 173 (21) | 185 (23) |
| Psychiatric disorders | 126 (15) | 122 (15) |
| Gastrointestinal disorders | 241 (29) | 236 (29) |
| Endocrine disorders | 26 (3) | 84 (10) |
| Gynecomastia in men† | 8 (1) | 55 (9)‡ |
| Breast pain in men† | 1 (0.1) | 10 (2)§ |
| Gynecomastia or breast pain in men† | 9 (1) | 61 (10)‡ |
| Edema | 21 (2) | 18 (2) |
| Serious hyperkalemia | 10 (1) | 14 (2) |

Effect of Spironolactone on PIIINP and Mortality

A sample of 253 patients from within the study group participated in a substudy (CHF NYHA III and IV, mean age 69, left ventricular ejection fraction ("LVEF")=26%, ischemic heart disease=46%, all were on conventional therapy, 92% on ACE inhibitors). Patients were randomized to placebo or spironolactone 15.5 to 50 mg/day. Serum PIIINP was measured at baseline and 6 months after randomization. Mean survival was 24 months.

Baseline serum PIIINP level was 4.6 (s.d.=2.5) and was similar in the spironolactone and placebo group. At 6 months, PIIINP decreased in the spironolactone from 4.9 (s.d.=2.7) to 4.1 (s.d.=1.9) (p=0.005), but not in the placebo group (p=0.65). Baseline levels above the 95% CL of controls (>4.2 μg/l) were associated with an increased risk of death in the placebo group (RR=1.89 [1.12–3.2](p=0.01)), but not in the spironolactone group (RR=0.69[0.45–1.36](p=0.39)). More marked survival benefit of spironolactone treatment was observed in patients with a baseline PIIINP >4.2 μg/l as compared to patients with lower baseline levels of PIIINP (RR=0.54 [0.33–0.88](p<0.02) vs. 1.37 [0.78–2.31](p=0.28). The mortality relative risk reduction was 33% in the high risk group. These findings were unchanged after adjustment for other prognostic factors (NYHA class, serum creatinine and age).

It is suggested by these studies that in patients with CHF, elevated serum PIIINP was significantly associated with excess mortality. Spironolactone decreased serum PIIINP and suggested that the beneficial effect of spironolactone on survival in patients with CHF may be explained, in part, by the lowering extracellular matrix production or turnover.

Spironolactone Effect to Lower Brain Natriuretic Peptide Levels is Associated With Reduced Risk of Mortality A sample of 107 patients from within the study group group participated in a substudy (NYHA III–IV), mean LVEF 25%). Patients received standard CHF therapy and 25 mg/day spironolactone or placebo. Brain Natriuretic Peptide (BNP) levels were measured at baseline and 3 and 6 months after therapy. Results were expressed in pg/ml, geometric mean [95%CL] and data were compared using a Mann-Whitney-Wilcoxon test.

TABLE 6

Effect of Spironolactone on BNP levels

| | Placebo (n = 53) | Spironolactone (n = 54) | p value |
|---|---|---|---|
| T0 | 74 [64–85] | 67 [59–76] | 0.33 |
| T3 | 68 [49–78] | 52 [45–61] | 0.02 |
| T6 | 64 [54–76] | 52 [44–61] | 0.09 |
| T3/T0 | 0.99 | 0.77 | 0.004 |
| T6/T0 | 0.96 | 0.77 | 0.05 |

Thus, Spironolactone treatment, which results in a significant decrease in fatalities and non-fatal hospitalizations, also results in a decrease in BNP levels and may reflect the beneficial effect on the left ventricular remodeling though the reduction of myocardial stretching.

TABLE 7

Relative Risk of Reduction in Mortality Analyzed by Baseline Characteristics

| Patients | Risk Reduction with SPironolactone | significance |
|---|---|---|
| LVEF of ≦21% | 25% | p = 0.034 |
| LVEF 22–29% | 26% | p = 0.020 |
| LVEF 30–50% | 37% | p = 0.011 |
| NYHA Class III heart failure | 28% | p < 0.0008 |
| NYHA Class IV heart failure | 29% | p < 0.0098 |
| ischemic heart failure | 28% | p < 0.0012 |
| nonischemic heart failure | 32% | p < 0.0016 |

Dosing Based on Natriuretic Peptides and PIIINP

The natriuretic peptides are a group of structurally similar but genetically distinct peptides that have diverse actions in cardiovascular, renal, and endocrine homeostasis. Atrial natriuretic peptide (ANP) and brain natriuretic peptide (BNP) are of myocardial cell origin and C-type natriuretic peptide (CNP) is of endothelial origin. ANP and BNP bind to the natriuretic peptide-A receptor (NPR-A), which, via 3',5'-cyclic guanosine monophosphate (cGMP), mediates natriuresis, vasodilation, renin inhibition, antimitogenesis, and lusitropic properties.

ANP is thought to play a role in renal regulation of salt balance by reducing tubular reabsorption of sodium and chloride. ANP can excite cardiac nerve endings and invoke a decrease in arterial blood pressure and a reduction in renal sympathetic nerve activity. Congestive heart failure represents a pathological state in which the activation of the natriuretic peptides exceeds those of all other states and is associated with poor long-term prognosis in heart failure.

Atrial natriuretic factor (ANF) production is induced in the ventricle under pathological circumstances and after exposure to hypertrophic agents including the α-adrenergic agonist phenylephrine. Release of ANF is significantly under conditions of hypertension and infarction. Even though ventricular natriuretic factor (ANF) has been considered to be a specific molecular marker of hypertrophy, its role in hypertrophy is unclear. Levin, E. R., Gardner, D. G., and Samson, W. K. (1998) *N. Engl. J. Med.* 339, 321–328

Extracellular matrix turnover is one of the determinants of vascular constrictive remodeling and may be monitored by measuring the blood level of procollagen type III aminoterminal propeptide ("PIIINP"). In congestive heart failure, extracellular matrix turnover is a major determinant of cardiac remodeling, diastolic function and pumping capacity.

Accordingly, dosing of therapeutic agents for congestive heart disease may be determined and adjusted based on measurement of blood concentrations of PIIINP, ANF, ANP, or BNP. A decrease in blood PIIINP level relative to baseline PIIINP level prior to administration of the aldosterone antagonist and during administration indicate a decrease in extracellular matrix turnover and therefore provides a correlation with inhibition of congestive heart disease. Similarly, levels of ANF, ANP, and BNP and may be relative to baseline levels prior to administration of the aldosterone antagonist and during administration to indicate levels of efficacy.

Administration of the angiotensin converting enzyme inhibitor and the aldosterone antagonist may take place sequentially in separate formulations, or may be accomplished by simultaneous administration in a single formulation or separate formulations. Administration may be accomplished by oral route, or by intravenous, intramuscular or subcutaneous injections. The formulation may be in the form of a bolus, or in the form of aqueous or non-aqueous isotonic sterile injection solutions or suspensions. These solutions and suspensions may be prepared from sterile powders or granules having one or more pharmaceutically-acceptable carriers or diluents, or a binder such as gelatin or hydroxypropyl-methyl cellulose, together with one or more of a lubricant, preservative, surface-active or dispersing agent.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The ACE inhibitor may be present in an amount from about 1 to 200 mg, preferably from about 2 to 150 mg, depending upon the specific ACE inhibitor selected. A suitable daily dose for a mammal may vary widely depending on the condition of the patient and other factors. The ALDO antagonist may be present in an amount of from about 1 to 400 mg, preferably from about 2 to 150 mg, depending upon the specific ALDO antagonist compound selected and the specific disease state being targeted for the combination therapy.

For disease states which require prevention, reduction or treatment of a cardiovascular disease state without incidence of hyperkalemia, for example, the ALDO antagonist component, typically spironolactone, will be present in the combination therapy in an amount in a range from about 1 mg to about 25 mg per dose per day.

Examples of various fixed combinations of ACE inhibitor and ALDO antagonist representing a "double therapy" of the invention are as follows;

| ACE Inhibitor | | ALDO Antagonist | |
| --- | --- | --- | --- |
| Captopril(mg)[1] | Enalapril(mg)[1] | Lisinopril(mg)[2] | Spironolactone(mg)[2] |
| 7.5 to 30 | 2.5 to 20 | 5 to 20 | 5 |
| 7.5 to 30 | 2.5 to 20 | 5 to 20 | 7.5 |
| 7.5 to 30 | 2.5 to 20 | 5 to 20 | 10 |
| 7.5 to 30 | 2.5 to 20 | 5 to 20 | 12.5 |
| 7.5 to 30 | 2.5 to 20 | 5 to 20 | 15 |
| 7.5 to 30 | 2.5 to 20 | 5 to 20 | 17.5 |
| 7.5 to 30 | 2.5 to 20 | 5 to 20 | 20 |
| 7.5 to 30 | 2.5 to 2C | 5 to 20 | 22.5 |
| 7.5 to 30 | 2.5 to 20 | 5 to 20 | 25 |
| 7.5 to 30 | 2.5 to 20 | 5 to 20 | 50 |

[1]Dose given 2 times per day
[2]Dose given once per day

The present invention further comprises a composition comprising an angiotensin converting enzyme inhibitor, an aldosterone antagonist, a loop diuretic and digoxin, and the pharmaceutically acceptable salts, esters and prodrugs thereof. Preferably, the composition comprises a first amount of an angiotensin converting enzyme inhibitor, or a pharmaceutically acceptable salt, ester or prodrug thereof; a second amount of an aldosterone antagonist, or a pharmaceutically acceptable salt, ester or prodrug thereof; a third amount of a loop diuretic, or a pharmaceutically acceptable salt, ester or prodrug thereof; a fourth amount of digoxin, or a pharmaceutically acceptable salt, ester or prodrug thereof; and a pharmaceutically acceptable carrier; wherein the first, second, third and fourth amounts in combination comprise a therapeutically effective amount of said inhibitor, antagonist, loop diuretic and digoxin. More preferably, the aldosterone antagonist is selected from spironolactone and eplerenone.

The active ingredients may also be administered by injection as a composition wherein, for example, saline, dextrose or water may be used as a suitable carrier.

The dosage regimen for treating a disease condition with the combination therapy of this invention is selected in accordance with a variety of factors, including the type, age, weight, sex and medical condition of the patient, the severity of the disease, the route of administration, and the particular compound employed, and thus may vary widely.

For therapeutic purposes, the active components of this combination therapy invention are ordinarily combined with one or more adjuvants appropriate to the indicated route of administration. If administered per os, the components may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxy-propylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The components may be dissolved in water, polyethylene glycol, propylene glycol, ethanol, corn oil, cottonseed oil, peanut oil, sesame oil, benzyl alcohol, sodium chloride, and/or various buffers. Other adjuvants and modes. of administration are well and widely known in the pharmaceutical art.

Pharmaceutical compositions for use in the treatment methods of the invention may be administered in oral form or by intravenous administration. Oral administration of the combination therapy is preferred. Dosing for oral administration may be with a regimen calling for single daily dose, or for a single dose every other day, or for multiple, spaced doses throughout the day. The active agents which make up the combination therapy may be administered simultaneously, either in a combined dosage form or in separate dosage forms intended for substantially simultaneous oral administration. The active agents which make up the combination therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to several hours, depending upon the properties of each active agent such a potency, solubility, bioavailability, plasma half-life and kinetic profile of the agent, as well as depending upon the age and condition of the patient. The active agents of the combined therapy whether administered simultaneously, substantially simultaneously, or sequentially, may involve a regimen calling for administration of one active agent by oral route and the other active agent by intravenous route. Whether the active agents of the combined therapy are administered by oral or intravenous route, separately or together, each such active agent will be contained in a suitable pharmaceutical formulation of pharmaceutically-acceptable excipients, diluents or other formulations components. Examples of suitable pharmaceutically-acceptable formulations containing the active components for oral administration are given below. Even though such formulations list both active agents together in the same recipe, it is appropriate for such recipe to be utilized for a formulation containing one of the active components.

EXAMPLE 1

An oral dosage may be prepared by screening and then mixing together the following list of ingredients in the amounts indicated. The dosage may then be placed in a hard gelatin capsule.

| Ingredients | Amounts |
|---|---|
| captopril | 62.0 mg |
| spironolactone | 12.5 mg |
| magnesium stearate | 10 mg |
| lactose | 100 mg |

EXAMPLE 2

An oral dosage may be prepared by mixing together and granulating with a 10% gelatin solution. The wet granules are screened, dried, mixed with starch, talc and stearic acid, screened and compressed into a tablet.

| Ingredients | Amounts |
|---|---|
| captopril | 62.0 mg |
| spironolactone | 12.5 mg |
| calcium sulfate dihydrate | 100 mg |
| sucrose | 15 mg |
| starch | 8 mg |
| talc | 4 mg |
| stearic acid | 2 mg |

EXAMPLE 3

An oral dosage may be prepared by screening and then mixing together the following list of ingredients in the amounts indicated. The dosage may then be placed in a hard gelatin capsule.

| Ingredients | Amounts |
|---|---|
| enalapril | 15 mg |
| spironolactone | 12.5 mg |
| magnesium stearate | 10 mg |
| lactose | 100 mg |

EXAMPLE 4

An oral dosage may be prepared by mixing together and granulating with a 10% gelatin solution. The wet granules are screened, dried, mixed with starch, talc and stearic acid, screened and compressed into a tablet.

| Ingredients | Amounts |
|---|---|
| enalapril | 15 mg |
| spironolactone | 12.5 mg |
| calcium sulfate dihydrate | 100 mg |
| sucrose | 15 mg |
| starch | 8 mg |
| talc | 4 mg |
| stearic acid | 2 mg |

EXAMPLE 5

An oral dosage may be prepared by screening and then mixing together the following list of ingredients in the amounts indicated. The dosage may then be placed in a hard gelatin capsule.

| Ingredients | Amounts |
|---|---|
| lisinopril | 15 mg |
| spironolactone | 12.5 mg |
| magnesium stearate | 10 mg |
| lactose | 100 mg |

EXAMPLE 6

An oral dosage may be prepared by mixing together and granulating with a 10% gelatin solution. The wet granules are screened, dried, mixed with starch, talc and stearic acid, screened and compressed into a tablet.

| Ingredients | Amounts |
| --- | --- |
| lisinopril | 15 mg |
| spironolactone | 12.5 mg |
| calcium sulfate dihydrate | 100 mg |
| sucrose | 15 mg |
| starch | 8 mg |
| talc | 4 mg |
| stearic acid | 2 mg |

Although this invention has been described with respect to specific embodiments, the details of these embodiments are not to be construed as limitations.

EXAMPLE 7

An oral dosage may be prepared by screening and then mixing together the following list of ingredients in the amounts indicated. The dosage may then be placed in a hard gelatin capsule.

| Ingredients | Amounts |
| --- | --- |
| lisinopril | 15 mg |
| spironolactone | 12.5 mg |
| furosemide | 73.9 mg |
| magnesium stearate | 10 mg |
| lactose | 100 mg |

EXAMPLE 8

An oral dosage may be prepared by screening and then mixing together the following list of ingredients in the amounts indicated. The dosage may then be placed in a hard gelatin capsule.

| Ingredients | Amounts |
| --- | --- |
| lisinopril | 15 mg |
| spironolactone | 12.5 mg |
| furosemide | 73.9 mg |
| digoxin | 75 µg |
| magnesium stearate | 10 mg |
| lactose | 100 mg |

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Although this invention has been described with respect to specific embodiments, the details of these embodiments are not to be construed as limitations.

What is claimed is:

1. A co-therapy method for treating a cardiovascular disorder in a subject comprising administering a first amount of an angiotensin converting enzyme inhibitor and a second amount of eplerenone to the subject, wherein the first amount and second amount together comprise a therapeutically effective amount of the inhibitor and eplerenone.

2. The method of claim 1 wherein the angiotensin converting enzyme inhibitor is selected from the group consisting of alacepril, benazepril, captopril, cilazapril, delapril, enalapril, enalaprilat, fosinopril, fosinoprilat, imidapril, lisinopril, perindopril, quinapril, ramipril, saralasin acetate, temocapril, trandolapril, ceranapril, moexipril, quinaprilat, spirapril, Bioproject BP1.137, Chiesi CHF 1514, Fisons FPL-66564, idrapril, Marion Merrell Dow MDL-100240, perindoprilat and Servier S-5590.

3. The method of claim 2 wherein the angiotensin converting enzyme inhibitor is selected from the group consisting of alacepril, benazepril, captopril, cilazapril, delapril, enalapril, enalaprilat, fosinopril, fosinoprilat, imidapril, lisinopril, perindopril, quinapril, ramipril, saralasin acetate, temocapril, trandolapril, ceranapril, moexipril, quinaprilat and spirapril.

4. The method of claim 1 wherein the angiotensin converting enzyme inhibitor is benazepril, or a pharmaceutically acceptable salt, ester or prodrug thereof.

5. The method of claim 1 wherein the angiotensin converting enzyme inhibitor is moexipril, or a pharmaceutically acceptable salt, ester or prodrug thereof.

6. The method of claim 1 wherein the angiotensin converting enzyme inhibitor is perindopril, or a pharmaceutically acceptable salt, ester or prodrug thereof.

7. The method of claim 1 wherein the angiotensin converting enzyme inhibitor is quinapril, or a pharmaceutically acceptable salt, ester or prodrug thereof.

8. The method of claim 1 wherein the angiotensin converting enzyme inhibitor is ramipril, or a pharmaceutically acceptable salt, ester or prodrug thereof.

9. The method of claim 1 wherein the angiotensin converting enzyme inhibitor is trandolapril, or a pharmaceutically acceptable salt, ester or prodrug thereof.

10. The method of claim 1 wherein the angiotensin converting enzyme inhibitor is cilazapril, or a pharmaceutically acceptable salt, ester or prodrug thereof.

11. The method of claim 1 wherein the angiotensin converting enzyme inhibitor is fosinopril, or a pharmaceutically acceptable salt, ester or prodrug thereof.

12. The method of claim 1 wherein the angiotensin converting enzyme inhibitor is spirapril, or a pharmaceutically acceptable salt, ester or prodrug thereof.

13. The method of claim 1 wherein the angiotensin converting enzyme inhibitor is enalapril, or a pharmaceutically acceptable salt, ester or prodrug thereof.

14. The method of claim 13 wherein the angiotensin converting enzyme inhibitor is administered in a daily dose range of about 5 mg to about 40 mg.

15. The method of claim 1 wherein the angiotensin converting enzyme inhibitor is lisinopril, or a pharmaceutically acceptable salt, ester or prodrug thereof.

16. The method of claim 15 wherein the angiotensin converting enzyme inhibitor is administered in a daily dose range of about 5 mg to about 20 mg.

17. The method of claim 1 wherein the angiotensin converting enzyme inhibitor and eplerenone are administered in a weight ratio range from about 0.1-to-one to about twenty-five-to-one of the angiotensin converting enzyme inhibitor to eplerenone.

18. The method of claim 17 wherein the weight ratio range is from about 0.5-to-one to about fifteen-to-one.

19. The method of claim 17 wherein the weight ratio range is from about 0.5-to-one to about five-to-one.

20. The method of claim 1 wherein eplerenone is administered in a daily dose range from about 0.5 mg to about 500 mg.

21. The method of claim 1 wherein the angiotensin converting enzyme inhibitor and eplerenone are administered in a sequential manner.

22. The method of claim 1 wherein angiotensin converting enzyme inhibitor and eplerenone are administered in a substantially simultaneous manner.

23. The method of claim 1 wherein the angiotensin converting enzyme inhibitor and eplerenone are administered at doses that in combination result in a reduction in the rate of deaths as compared to monotherapy with an angiotensin converting enzyme inhibitor.

24. The method of claim 1 wherein the angiotensin converting enzyme inhibitor and eplerenone are administered at doses that in combination result in a reduction in the number of non-fatal hospitalizations as compared to monotherapy with an angiotensin converting enzyme inhibitor.

25. The method of claim 1 wherein the angiotensin converting enzyme inhibitor and eplerenone are administered at doses that in combination result in a reduction in the rate of deaths resulting from sudden death in subjects afflicted with or susceptible to elevated heart rate variability as compared to monotherapy with an angiotensin converting enzyme inhibitor.

26. The method of claim 1 wherein the angiotensin converting enzyme inhibitor and eplerenone are administered at doses that in combination result in a reduction in the rate of deaths resulting from progression of heart failure as compared to monotherapy with an angiotensin converting enzyme inhibitor.

27. The method of claim 1 wherein the angiotensin converting enzyme inhibitor and eplerenone are administered at doses that in combination result in a reduction in the rate of deaths or the number of non-fatal hospitalizations in subjects having a left ventricular ejection fraction greater than about 26% as compared to monotherapy with an angiotensin converting enzyme inhibitor.

28. The method of claim 1 wherein the angiotensin converting enzyme inhibitor and eplerenone are administered at doses that in combination result in a reduction in the rate of deaths or the number of non-fatal hospitalizations in subjects having a left ventricular ejection fraction less than about 26% as compared to monotherapy with an angiotensin converting enzyme inhibitor.

29. The method of claim 1 wherein the angiotensin converting enzyme inhibitor and eplerenone are administered at doses that in combination suppress clinically significant cough due to a respiratory tract disorder selected from the group consisting of elevated pulmonary arterial fibrosis, pulmonary edema and pleural effusion as compared to monotherapy with an angiotensin converting enzyme inhibitor.

30. The method of claim 1 wherein the angiotensin converting enzyme inhibitor and eplerenone are administered at doses that in combination result in a reduction in the blood level of N-terminal atrial natriuretic factor in the subject.

31. The method of claim 1 wherein the angiotensin converting enzyme inhibitor and eplerenone are administered at doses that in combination result in a reduction in the blood level of procollagen type III aminoterminal propeptide in the subject.

32. The method of claim 1 wherein the angiotensin converting enzyme inhibitor and eplerenone are administered at doses that in combination result in an increase in the left ventricular ejection fraction in the subject as compared to monotherapy with an angiotensin converting enzyme inhibitor.

33. The method of claim 1 wherein the subject is a human.

34. The method of claim 1 wherein the subject is susceptible to sudden death.

35. The method of claim 1 wherein the subject is classified in New York Heart Association class III or class IV prior to combination therapy.

36. The method of claim 1 wherein the subject has a left ventricular ejection fraction greater than about 26%.

37. The method of claim 1 wherein the subject has a left ventricular ejection fraction less than about 26%.

38. The method of claim 1 wherein the subject is susceptible to or suffering from clinically significant cough due to a respiratory tract disorder selected from the group consisting of elevated pulmonary arterial fibrosis, pulmonary edema and pleural effusion.

39. A co-therapy method for treating a cardiovascular disorder in a subject comprising administering a first amount of an angiotensin converting enzyme inhibitor, a second amount of a diuretic, and a third amount of eplerenone to the subject,
   wherein the first, second and third amounts together comprise a therapeutically effective amount of the inhibitor, diuretic and eplerenone; and
   wherein the diuretic has no substantial aldosterone antagonist effect.

40. The method of claim 39 wherein the angiotensin converting enzyme inhibitor is selected from the group consisting of alacepril, benazepril, captopril, cilazapril, delapril, enalapril, enalaprilat, fosinopril, fosinoprilat, imidapril, lisinopril, perindopril, quinapril, ramipril, saralasin acetate, temocapril, trandolapril, ceranapril, moexipril, quinaprilat, spirapril, Bioproject BP1.137, Chiesi CHF 1514, Fisons FPL-66564, idrapril, Marion Merrell Dow MDL-100240, perindoprilat and Servier S-5590.

41. The method of claim 40 wherein the angiotensin converting enzyme inhibitor is selected from the group consisting of alacepril, benazepril, captopril, cilazapril, delapril, enalapril, enalaprilat, fosinopril, fosinoprilat, imidapril, lisinopril, perindopril, quinapril, ramipril, saralasin acetate, temocapril, trandolapril, ceranapril, moexipril, quinaprilat and spirapril.

42. The method of claim 39 wherein the angiotensin converting enzyme inhibitor is benazepril, or a pharmaceutically acceptable salt, ester or prodrug thereof.

43. The method of claim 39 wherein the angiotensin converting enzyme inhibitor is moexipril, or a pharmaceutically acceptable salt, ester or prodrug thereof.

44. The method of claim 39 wherein the angiotensin converting enzyme inhibitor is perindopril, or a pharmaceutically acceptable salt, ester or prodrug thereof.

45. The method of claim 39 wherein the angiotensin converting enzyme inhibitor is quinapril, or a pharmaceutically acceptable salt, ester or prodrug thereof.

46. The method of claim 39 wherein the angiotensin converting enzyme inhibitor is ramipril, or a pharmaceutically acceptable salt, ester or prodrug thereof.

47. The method of claim 39 wherein the angiotensin converting enzyme inhibitor is trandolapril, or a pharmaceutically acceptable salt, ester or prodrug thereof.

48. The method of claim 39 to wherein the angiotensin converting enzyme inhibitor is cilazapril, or a pharmaceutically acceptable salt, ester or prodrug thereof.

49. The method of claim 39 wherein the angiotensin converting enzyme inhibitor is fosinopril, or a pharmaceutically acceptable salt, ester or prodrug thereof.

50. The method of claim 39 wherein the angiotensin converting enzyme inhibitor is spirapril, or a pharmaceutically acceptable salt, ester or prodrug thereof.

51. The method of claim 39 wherein the angiotensin converting enzyme inhibitor is enalapril, or a pharmaceutically acceptable salt, ester or prodrug thereof.

52. The method of claim 51 wherein the angiotensin converting enzyme inhibitor is administered in a daily dose range of about 5 mg to about 40 mg.

53. The method of claim 39 wherein the angiotensin converting enzyme inhibitor is lisinopril, or a pharmaceutically acceptable salt, ester or prodrug thereof.

54. The method of claim 53 wherein the angiotensin converting enzyme inhibitor is administered in a daily dose range of about 5 mg to about 20 mg.

55. The method of claim 39 wherein the angiotensin converting enzyme inhibitor and eplerenone are administered in a weight ratio range from about 0.1-to-one to about twenty-five-to-one of the angiotensin converting enzyme inhibitor to eplerenone.

56. The method of claim 55 wherein the weight ratio range is from about 0.5-to-one to about fifteen-to-one.

57. The method of claim 55 wherein the weight ratio range is from about 0.5-to-one to about five-to-one.

58. The method of claim 39 wherein eplerenone is administered in a daily dose range from about 0.5 mg to about 500 mg.

59. The method of claim 39 wherein the angiotensin converting enzyme inhibitor, diuretic and eplerenone are administered in a sequential manner.

60. The method of claim 39 wherein the angiotensin converting enzyme inhibitor, diuretic and eplerenone are administered in a substantially simultaneous manner.

61. The method of claim 39 wherein the angiotensin converting enzyme inhibitor, diuretic and eplerenone are administered at doses that in combination result in a reduction in the rate of deaths as compared to monotherapy with an angiotensin converting enzyme inhibitor.

62. The method of claim 39 wherein the angiotensin converting enzyme inhibitor, diuretic and eplerenone are administered at doses that in combination result in a reduction in the number of non-fatal hospitalizations as compared to monotherapy with an angiotensin converting enzyme inhibitor.

63. The method of claim 39 wherein the angiotensin converting enzyme inhibitor, diuretic and eplerenone are administered at doses that in combination result in a reduction in the rate of deaths resulting from sudden death in subjects afflicted with or susceptible to elevated heart rate variability as compared to monotherapy with an angiotensin converting enzyme inhibitor.

64. The method of claim 39 wherein the angiotensin converting enzyme inhibitor, diuretic and eplerenone are administered at doses that in combination result in a reduction in the rate of deaths resulting from progression of heart failure as compared to monotherapy with an angiotensin converting enzyme inhibitor.

65. The method of claim 39 wherein the angiotensin converting enzyme inhibitor, diuretic and eplerenone are administered at doses that in combination result in a reduction in the rate of deaths or the number of non-fatal hospitalizations in subjects having a left ventricular ejection fraction greater than about 26% as compared to monotherapy with an angiotensin converting enzyme inhibitor.

66. The method of claim 39 wherein the angiotensin converting enzyme inhibitor, diuretic and eplerenone are administered at doses that in combination result in a reduction in the rate of deaths or the number of non-fatal hospitalizations in subjects having a left ventricular ejection fraction less than about 26% as compared to monotherapy with an angiotensin converting enzyme inhibitor.

67. The method of claim 39 wherein the angiotensin converting enzyme inhibitor, diuretic and eplerenone are administered at doses that in combination suppress clinically significant cough due to a respiratory tract disorder selected from the group consisting of elevated pulmonary arterial fibrosis, pulmonary edema and pleural effusion as compared to monotherapy with an angiotensin converting enzyme inhibitor.

68. The method of claim 39 wherein the angiotensin converting enzyme inhibitor, diuretic and eplerenone are administered at doses that in combination result in a reduction in the blood level of N-terminal atrial natriuretic factor in the subject.

69. The method of claim 39 wherein the angiotensin converting enzyme inhibitor, diuretic and eplerenone are administered at doses that in combination result in a reduction in the blood level of procollagen type III aminoterminal propeptide in the subject.

70. The method of claim 39 wherein the angiotensin converting enzyme inhibitor, diuretic and eplerenone are administered at doses that in combination result in an increase in the left ventricular ejection fraction in the subject as compared to monotherapy with an angiotensin converting enzyme inhibitor.

71. The method of claim 39 wherein the subject is a human.

72. The method of claim 39 wherein the subject is susceptible to sudden death.

73. The method of claim 39 wherein the subject is classified in New York Heart Association class III or class IV prior to combination therapy.

74. The method of claim 39 wherein the subject has a left ventricular ejection fraction greater than about 26%.

75. The method of claim 39 wherein the subject has a left ventricular ejection fraction less than about 26%.

76. The method of claim 39 wherein the subject is susceptible to or suffering from clinically significant cough due to a respiratory tract disorder selected from the group consisting of elevated pulmonary arterial fibrosis, pulmonary edema and pleural effusion.

77. The method of claim 39 comprising administering a fourth amount of digoxin, wherein the first, second, third and fourth amounts together comprise a therapeutically effective amount of the angiotensin converting enzyme inhibitor, eplerenone, diuretic and digoxin.

78. The method of claim 71 wherein the angiotensin converting enzyme inhibitor, eplerenone, diuretic, and digoxin are administered at doses that in combination result in a reduction in the rate of deaths as compared to monotherapy with an angiotensin converting enzyme inhibitor.

79. The method of claim 77 wherein the angiotensin converting enzyme inhibitor, eplerenone, diuretic, and digoxin are administered at doses that in combination result in a reduction in the number of non-fatal hospitalizations as compared to monotherapy with an angiotensin converting enzyme inhibitor.

80. The method of claim 77 wherein the angiotensin converting enzyme inhibitor, eplerenone, diuretic, and digoxin are administered at doses that in combination result in a reduction in the blood level of N-terminal atrial natriuretic factor in the subject.

81. The method of claim 77 wherein the angiotensin converting enzyme inhibitor, eplerenone, diuretic, and digoxin are administered at doses that in combination result in a reduction in the blood level of procollagen type III aminoterminal propeptide in the subject.

82. The method of claim 77 wherein the angiotensin converting enzyme inhibitor, eplerenone, diuretic, and digoxin are administered at doses that in combination result in an increase in the left ventricular ejection fraction in the subject as compared to monotherapy with an angiotensin converting enzyme inhibitor.

83. A composition comprising an angiotensin converting enzyme inhibitor and eplerenone.

84. The composition of claim 83 comprising:

a first amount of an angiotensin converting enzyme inhibitor;

a second amount of eplerenone; and a pharmaceutically acceptable carrier.

85. The composition of claim 84 wherein the angiotensin converting enzyme inhibitor is selected from the group consisting of alacepril, benazepril, captopril, cilazapril, delapril, enalapril, enalaprilat, fosinopril, fosinoprilat, imidapril, lisinopril, perindopril, quinapril, ramipril, saralasin acetate, temocapril, trandolapril, ceranapril, moexipril, quinaprilat, spirapril, Bioproject BP1.137, Chiesi CHF 1514, Fisons FPL-66564, idrapril, Marion Merrell Dow MDL-100240, perindoprilat and Servier S-5590.

86. The composition of claim 85 wherein the angiotensin converting enzyme inhibitor is selected from the group consisting of alacepril, benazepril, captopril, cilazapril, delapril, enalapril, enalaprilat, fosinopril, fosinoprilat, imidapril, lisinopril, perindopril, quinapril, ramipril, saralasin acetate, temocapril, trandolapril, ceranapril, moexipril, quinaprilat and spirapril.

87. The composition of claim 84 wherein the angiotensin converting enzyme inhibitor is benazepril, or a pharmaceutically acceptable salt, ester or prodrug thereof.

88. The composition of claim 84 wherein the angiotensin converting enzyme inhibitor is moexipril, or a pharmaceutically acceptable salt, ester or prodrug thereof.

89. The composition of claim 84 wherein the angiotensin converting enzyme inhibitor is perindopril, or a pharmaceutically acceptable salt, ester or prodrug thereof.

90. The composition of claim 84 wherein the angiotensin converting enzyme inhibitor is quinapril, or a pharmaceutically acceptable salt, ester or prodrug thereof.

91. The composition of claim 84 wherein the angiotensin converting enzyme inhibitor is ramipril, or a pharmaceutically acceptable salt, ester or prodrug thereof.

92. The composition of claim 84 wherein the angiotensin converting enzyme inhibitor is trandolapril, or a pharmaceutically acceptable salt, ester or prodrug thereof.

93. The composition of claim 84 wherein the angiotensin converting enzyme inhibitor is cilazapril, or a pharmaceutically acceptable salt, ester or prodrug thereof.

94. The composition of claim 84 wherein the angiotensin converting enzyme inhibitor is fosinopril, or a pharmaceutically acceptable salt, ester or prodrug thereof.

95. The composition of claim 84 wherein the angiotensin converting enzyme inhibitor is spirapril, or a pharmaceutically acceptable salt, ester or prodrug thereof.

96. The composition of claim 84 wherein the angiotensin converting enzyme inhibitor is enalapril, or a pharmaceutically acceptable salt, ester or prodrug thereof.

97. The composition of claim 96 wherein the angiotensin converting enzyme inhibitor is administered in a daily dose range of about 5 mg to about 40 mg.

98. The composition of claim 84 wherein the angiotensin converting enzyme inhibitor is lisinopril, or a pharmaceutically acceptable salt, ester or prodrug thereof.

99. The composition of claim 98 wherein the angiotensin converting enzyme inhibitor is administered in a daily dose range of about 5 mg to about 20 mg.

100. The composition of claim 84 wherein the angiotensin converting enzyme inhibitor and eplerenone are administered in a weight ratio range from about 0.1-to-one to about twenty-five-to-one of the angiotensin converting enzyme inhibitor to eplerenone.

101. The composition of claim 100 wherein the weight ratio range is from about 0.5-to-one to about fifteen-to-one.

102. The composition of claim 101 wherein the weight ratio range is from about 0.5-to-one to about five-to-one.

103. The composition of claim 84 wherein eplerenone is administered in a daily dose range from about 0.5 mg to about 500 mg.

104. The composition of claim 84 further comprising a third amount of a diuretic.

105. The composition of claim 104 further comprising a fourth amount of digoxin.

* * * * *